(12) United States Patent
Kuzeff

(10) Patent No.: US 8,071,630 B2
(45) Date of Patent: Dec. 6, 2011

(54) TREATMENT OF EFFECT OF CHEMICALS WITH THEIR ULTRADILUTE STEREOISOMERS

(76) Inventor: Reinhard Michael Kuzeff, Moe (AU)

( * ) Notice: Subject to any disclaimer, the term of this patent is extended or adjusted under 35 U.S.C. 154(b) by 1207 days.

(21) Appl. No.: 10/505,956

(22) PCT Filed: Feb. 28, 2003

(86) PCT No.: PCT/AU03/00219
§ 371 (c)(1),
(2), (4) Date: Aug. 27, 2004

(87) PCT Pub. No.: WO03/072105
PCT Pub. Date: Sep. 4, 2003

(65) Prior Publication Data
US 2005/0119350 A1   Jun. 2, 2005

(30) Foreign Application Priority Data

Feb. 28, 2002 (AU) .......................... PS 0796
Mar. 6, 2002 (AU) .......................... PS 0925
Jul. 22, 2002 (AU) ............................ 2002950351
Jan. 24, 2003 (AU) ............................ 2003900353
Feb. 19, 2003 (AU) ............................ 2003900716

(51) Int. Cl.
*A61K 31/44* (2006.01)
*A61K 31/12* (2006.01)
*A61K 31/04* (2006.01)

(52) U.S. Cl. .......................... 514/343; 514/675; 514/740

(58) Field of Classification Search .................. 514/343, 514/675, 740
See application file for complete search history.

(56) References Cited

U.S. PATENT DOCUMENTS

| | | | |
|---|---|---|---|
| 3,432,545 A | 3/1969 | Howe | |
| 3,534,085 A | 10/1970 | Narayanan et al. | |
| 3,947,592 A | 3/1976 | Grosz | |
| 4,346,106 A | 8/1982 | Sudilovsky | |
| 6,239,105 B1 * | 5/2001 | Brewitt | 514/12 |
| 2008/0039523 A1 * | 2/2008 | Albert et al. | 514/494 |

FOREIGN PATENT DOCUMENTS

| | | |
|---|---|---|
| DE | 3829442 | 3/1990 |
| GB | A-1 277601 | 6/1972 |
| GB | 2141026 | 12/1984 |
| IE | 71050 | 1/1998 |
| WO | WO 91/00259 | 1/1991 |
| WO | WO 91 00259 | 10/1991 |
| WO | WO9814162 | 9/1998 |

OTHER PUBLICATIONS

Howe R & Shanks RG, "Optical Isomers of Propranolol," Nature, Jun. 1966, 210, 1336-1338.*
Stedman's Medical Dictionary 27th ed., Lippincott Williams & Wilkins, 2000, p. 827.*
Smith JG, "Organic Chemistry," 1st ed. McGraw Hill, Boston, 2006, p. 143.*
Armstrong DW, Wang X, and Ercal N, "Enantiomeric Composition of Nicotine in Smokeless Tobacco, Medicinal Products, and Commerical Reagents," Chirality, 1998, 10(7), 587-591.*
Hauora M. Guidelines for Prescribing Psychotropic Drugs. Minystry of Health, 1996.*
Farthing et al., J. Antimicrob. Chemother. "Effect of D-propanolol on Growth and Motility of Flagellate Protozoa," 1987, 20(4), pp. 519-522. Chemical Abstracts, vol. 107, 1987, Abstract 232966a.
Chasin et al., J. Biol. Chem., "—and—Adrenergic Receptors as Mediators of Accumulation of Cyclic Adenosine 3',5'—Monophosphate in Specific Areas of Guinea Pig Brain," vol. 246, No. 9, issued May 10, 1971, pp. 3037-3041.
Grimes et al., Invest. Ophthalmol. "Possible Cyclic Adenosine Monophosphate Mediation in Isoproterenol-induced Suppression of Cell Division in Rat Lens Epithelium," 1972, 11(4), pp. 231-235. Chemical Abstracts, vol. 77, 1972, Abstract 43303h.
Nilsson et al., Acta Endocrinol (Copenhagen), "Effects of Propranolol and Atenolol on Plasma and Urinary Cyclic Adenosine 3',5'—Monophosphate in Hyperthyroid Patients," 1980 94(1), pp. 38-45. Chemical Abstracts, vol. 93, 1980, Abstract 88913d.
Larsson P T et al: "Alpha and Beta-adrenergic influences . . . " Firbrinolysis, Churchill Livingston, London, GB, vol. 13. No. 4-5, Jul. 1999, pp. 169-175.
Jonas and Tortella: "Neuroprotection from glutamate toxicity with ultra-low dose glutamate", Neuroreport, Rapid Comms. GB vol. 12, NR-2, p. 335-339, Feb. 12, 2001.
Bonamin et al., Do Rio R G: "Very high dilutions of dexamethasone inhibit its pharmacological effects in vivo", British Homoeopathic J., Oct. 2001, vol. 90, 198-203.

* cited by examiner

*Primary Examiner* — San-Ming Hui
*Assistant Examiner* — Paul Zarek
(74) *Attorney, Agent, or Firm* — Christopher Wood; Premier Law Group, PLLC

(57) ABSTRACT

A method of treating an effect of a chemical agent, which agent is characterized by one or more chiral centres, by administering a dilution or an ultra-high dilution or potentised preparation of a stereoisomer of said chemical agent.

2 Claims, 8 Drawing Sheets

(R)-(+)-BAY K8644 and (S)-(-)-BAY K8644

(R)-(+)-BAY K8644 and (S)-(-)-BAY K8644

(R)-(+)α -Methylbenzyl isocyanate and
(S)-(-)α -Methylbenzyl isocyanate

| Parameters | |
|---|---|
| Placebo | |
| H1 | |
| H2 | |
| H3 | |
| | |
| Amplitude | |
| 0.1383 | |
| 0.1941 | |
| 0.1161 | |
| 0.1205 | |
| | |
| Final resting level | |
| 0.1366 | |
| 0.1470 | |
| 0.1256 | |
| 0.1188 | |
| | |
| Recovery Time | |
| 2.4810 | |
| 3.4518 | |
| 2.2293 | |
| 2.1932 | |

Note: H3 is freshly prepared replicate of H2

(R)-(+)α-Methylbenzyl isocyanate and
(S)-(-)α-Methylbenzyl isocyanate

C

| Parameters | |
|---|---|
| Placebo | |
| H1 | |
| H2 | |
| H3 | |
| | |
| Amplitude | |
| 0.1004 | |
| 0.1198 | |
| 0.1103 | |
| 0.1047 | |
| | |
| Final resting level | |
| <u>0.0801</u> | |
| <u>0.0697</u> | |
| <u>0.0550</u> | |
| <u>0.0506</u> | |
| | |
| Recovery Time | |
| <u>1.3287</u> | |
| 1.2752 | |
| <u>1.1709</u> | |
| 1.2233 | |

Note: H2=H3

(R)-(+)α -Methylbenzyl isocyanate and
(S)-(-)α -Methylbenzyl isocyanate

Racemic mixture of (R)-(+)α-Methylbenzyl isocyanate and (S)-(-)α-Methylbenzyl isocyanate (R)-(+)-VERAPAMIL and (S)-(-)-VERAPAMIL (R)-(+)-NICOTINE (+)-di-p-toluoyltartrate salt and (S)-(-)-NICOTINE

TREATMENT OF EFFECT OF CHEMICALS WITH THEIR ULTRADILUTE STEREOISOMERS

CROSS-REFERENCE TO RELATED APPLICATIONS

This application is the national phase under 35 U.S.C. §371 of prior PCT International Application No. PCT/AUO3/00219 filed Feb. 28, 2003.

FIELD OF THE INVENTION

The present invention relates to a method of treatment, in particular to a method of treating an effect of a chemical agent by administering a dilution or an ultra-high dilution or potentised preparation of a stereoisomer of the chemical agent.

The reference to any prior art in this specification is not, and should not be taken as, an acknowledgment or any form of suggestion that that prior art forms part of the common general knowledge in Australia.

Homoeopathy employs minute doses of usually harmful or toxic agents to stimulate organisms back to health. The agents used in homoeopathy are selected precisely on the basis of their ability to induce disease-like symptoms and signs in healthy people when administered in toxic doses, or one or more times in sub-harmful doses. These agents will in properly diluted form cure a sick person with similar symptoms. While microdose effects are now well accepted for example in the phenomenon known as hormesis, some homoeopathic solutions are attenuated beyond Avogadro's constant, i.e., in theory none of the original agent remains. Notwithstanding the apparent absurdity of homoeopathic dilutions there have been a great number of reported experiments which demonstrate that homoeopathic remedies are effective in treating a variety of symptoms.

SUMMARY OF THE INVENTION

Many chemical agents induce undesirable effects on organisms such as mammals. The effects which result from chemical agents having one or more chiral centres often result from a specific stereoisomer of the chemical agent. For example, (−)-adrenaline is the isomer which is found in humans and is the chemically active agent. It is about 15 times more active than (+)-adrenaline physiologically. Although chemically hard to differentiate in vitro, in vivo they are readily differentiated by the stereo-specificity of enzymes.

The inventors have now found that the effects of a chemical agent can be treated by administering a dilution or an ultra high dilution or potentised dilution of a stereoisomer of the chemical agent. Accordingly, there is provided a method of treatment of an organism suffering from the effects of a chemical agent having one or more chiral centres, said method comprising the steps of potentising a stereoisomer of said chemical agent, and administering said potentised stereoisomer to the organism.

Another aspect of the invention provides a method of treatment of an organism suffering from the effects of a chemical agent having one or more chiral centres, said method comprising the steps of diluting a stereoisomer of said chemical agent, and administering said diluted stereoisomer to the organism.

Still yet another aspect of the invention provides a method of treatment of an organism suffering from the effects of a chemical agent having one or more chiral centres, said method comprising the steps of diluting a stereoisomer of the chemical agent to an ultra-high dilution of said stereoisomer, and administering said ultra-high diluted stereoisomer to the organism.

However, the same effect may be obtained by using dilutions such as those used in investigations involving hormesis. Such dilutions exist below the toxic range of a given compound, substance or molecule. Such dilutions below the toxic range are stimulatory rather than toxic. Usually this phenomenon exists in a narrow range of concentrations just below the toxic range.

DETAILED DESCRIPTION OF THE PRESENT INVENTION

Figure 1A:
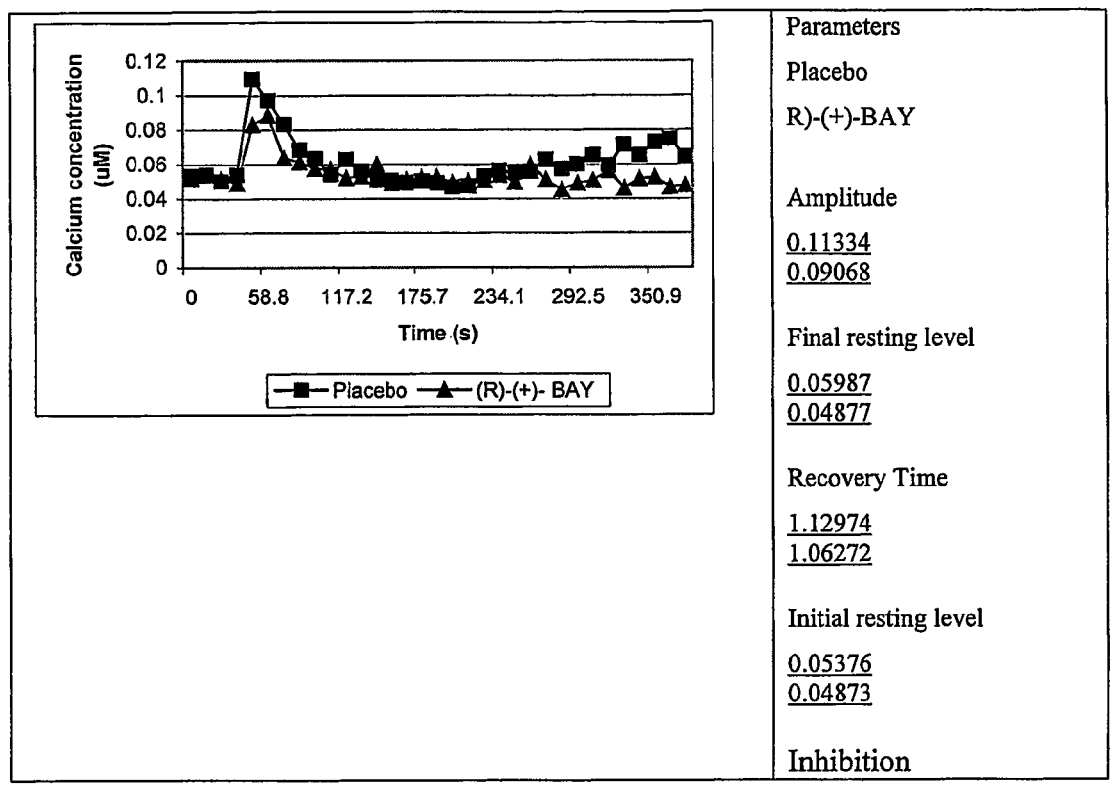
FIG. 1A shows the effect of preincubation of *Aspergillus awamori* with 10 µM (R)-(+)-BAY K8644 on $Ca^{2+}$ response to 10 µM (S)-(−)-BAY K8644.

In the context of the present invention it will be understood by those skilled in the art that the term "chemical agent" refers to one or more stereoisomers which induce the effect to be treated in the organism. The stereoisomer of the chemical agent which may be used to treat the effects of the chemical agent may be a stereoisomer which induces little or no effect in the organism of the type to be treated. For instance, where a compound has more than one stereoisomer which induces an undesirable effect and others are less active or inactive, then the stereoisomer which is administered to treat the undesirable effect is selected from the less active or inactive stereoisomers, preferably the enantiomer of the most active stereoisomer of the chemical agent. Alternatively, where all stereoisomers induce the undesirable effect to some extent it is preferred that the least active stereoisomer is selected although the other less active stereoisomers may also be effective in treating the undesirable effects of the chemical agent.

The method of the present invention may be used for the treatment of any organism, including for example, animals, plants and in particular, humans.

It is well known that chemical compounds which have one or more chiral centres form stereoisomers. Stereoisomers fall into two broad classes: optical isomers; and geometric (cis-trans) isomers. Optical isomers also fall into two groups, enantiomers and diastereoisomers. Accordingly, another aspect of the invention is a method of treating an effect of a chemical agent, which agent is characterized by one or more chiral centres, by administering a dilution or an ultra-high dilution or potentised preparation of a stereoisomer of said chemical agent wherein said stereoisomer is selected from the group consisting of enantiomers. While the selection of a less active stereoisomer for use in the method of the present invention may provide acceptable levels of treatment it is preferred that the enantiomer of the active stereoisomer be selected where possible. It has also been found where an optically active chemical agent is ionic or a salt, such as morphine sulfate, the stereoisomer, enantiomer etc. of the optically active ion or radical may be derived from other salts of the chemical agent or radical. For example, morphine hydrochloride may provide a suitable stereoisomer of morphine for the treatment of the effects of morphine sulfate. The stereoisomer selected to treat the effects of the chemical agent is potentised.

Where an optically active chemical agent is ionic or a salt, such as morphine sulfate or nicotine-di-p-toluoyltartrate salt, the stereoisomer, enantiomer etc. of the optically active non-ionic form or non-salt form of the chemical agent such as morphine or nicotine in non-ionic or non-salt form may be administered in suitably attenuated or diluted or potentised form. Further, where an optically active chemical agent is non-ionic or in a non-salt form, such as morphine or nicotine in the non-ionic or non-salt form, the stereoisomer, enantiomer etc. of the optically active ionic or salt form such as morphine sulfate or nicotine-di-p-toluoyltartrate salt may be administered in a suitably attenuated or diluted or potentised form.

Potentization of the stereoisomer may be according to the practices used in homoeopathy. Preferably the stereoisomer is potentised by succussion or trituration. Attenuation or dilution of the medicinal substance is, in homoeopathy, usually performed in the decimal, centesimal and fifty millesimal (LM) systems as the standard scales of attenuation, under which each successive attenuation contains just $\frac{1}{10}$, $\frac{1}{100}$ or $\frac{1}{50,000}$ as much of the medicinal substance as the preceding attenuation. It is preferred that after each attenuation, the attenuated medicinal substance is succussed (typically between 10 to 100 times at each stage of attenuation) or triturated. Generally, soluble substances may be subjected to succussion and insoluble or solid substances may be subjected to trituration.

In order to prepare the dilutions or potencies A ml of tincture or B grams of medicinal substance are added to C ml or D grams or E parts of vehicle. Subsequent liquid or solid attenuations are made by serial progression, succussing or triturating one part of the preceding attenuation to C ml, D grams or E parts of the vehicle respectively. A, B, C, D, and E, are any numbers greater than zero. When preparing consecutive attenuations, it is not necessary for A, B, C, D or E, to be kept constant. For example for the first, second, third, fourth, fifth, etc. attenuation, the values of A could be $A_1, A_2, A_3, A_4, A_5 \ldots$ etc., where $A_1, A_2, A_3, A_4, A_5 \ldots$ etc. represent any numbers greater than zero. The same principle applies for values of B, C, D, and E.

In the decimal scale of attenuation is generally practised one millilitre (1.0 ml) of tincture, one millilitre of 1× aqueous solution, or one gram (1.0 g) of 1× trituration represents 0.10 gram of dry crude medicinal substance. One millilitre of 2× attenuation, or one-gram (1.0 g) of 2nd trituration contains 0.01 gram of the dry crude medicinal substance. Subsequent liquid or solid attenuations are made by serial progression, succussing or triturating one (1) part of the preceding attenuation to nine (9) parts of the vehicle, and represent the following proportions of active principle (i.e. dried medicinal substance):

$$2X = 10^{-2}$$
$$3X = 10^{-3}$$
$$4X = 10^{-4}$$
$$5X = 10^{-5}$$
$$6X = 10^{-6}$$
$$7X = 10^{-7}$$
$$8X = 10^{-8}$$
(and so on . . . )

In decimal attenuations $nx=10^{-n}$ where n is an integer greater than 0. In the case of centesimal attenuations, each attenuation contains just one hundredth of the medicinal substance of the one before, $nC=10^{-2n}$. In the case of fifty millesimal attenuations one millilitre (1 ml) of the first fifty millesimal attenuation (1 LM) represents $4.0 \times 10^{-9}$ gram of dry crude medicinal substance. One millilitre (1 ml) of the second fifty millesimal attenuation (2 LM) represents $8.0 \times 10^{-14}$ gram of dry crude medicinal substance. Each subsequent attenuation represents a further decrease in concentration of dry crude medicinal substance by a factor of $2 \times 10^{-5}$. Each attenuation such as 2×, 3× or n× (2 C, 3 C or nC) (2 LM, 3 LM etc) is generally referred to as a potency.

In order to prepare the solid or liquid stereoisomers of chemical agents, it is effective to add 2 or more different potencies or attenuations together. A potency refers to a solution, which has undergone serial dilution and succussion and/or agitation whereas attenuation refers to a process of dilution, which may or may not involve succussion or agitation. The term potency also refers to solid attenuations as described herein. The term "different" potencies or attenuations encompasses 2 potencies or attenuations of different dilutions as well as solutions which have undergone a different number of steps of serial dilution or attenuation with succussion, or, in the case of solid attenuations, a different number of steps of serial trituration as described herein. For example, a person skilled in the art could add the fourth and twelfth potencies or attenuations together in equal or unequal quantities. The solution may then be succussed (shaken) N times, where N is any integer greater than zero. Alternatively, the solution is not succussed. Similarly, one could add the fourth, twelfth, or thirtieth potencies or attenuations together, or any number of combinations of potencies or attenuations.

Also, there is the situation where one could treat a racemic mixture with both the (+)- and (−)-enantiomers contemporaneously, either simultaneously or within the same course of treatment. This could be with a mixture of equal or unequal volumes of potencies or attenuations or dilutions or a combination of one or more of same or different potencies or attenuations of each enantiomer. This is illustrated in the discussion and non-limiting examples which follow:

For instance, one could mix one, two, three, four, five or more potencies, attenuations or dilutions of the (+)-enantiomer to one, two, three, four, five or more potencies of the (−)-enantiomer or vice versa. One or more potencies, attenuations or dilutions of an enantiomer may be prepared in one mixture, and added to an equal or unequal number of the same or different or any combination of potencies or attenuations of the other enantiomer prepared in a separate mixture. Alternatively, all potencies, attenuations or dilutions could be added to the same mixture.

(+)- and (−)-enantiomers may be mixed 50:50 or 25:75 or in any proportion. Thus, a mixture could be prepared by adding 2 ml of 4th, 12th and 30th potencies of (+)-enantiomer to 2 ml of 4th, 12th and 30th potencies of (−)-enantiomer, or vice versa. Alternatively 0.5 ml of 4th, 2 ml of 12th and 3.4 ml of 30th potencies could be used, and in fact the numbers 0.5, 2 and 3.4 could be replaced by any numbers greater than zero or equal to zero. Also, the 4th, 12th and 30th potencies could be replaced by any potencies represented by integers greater than or equal to 1. The mixtures of (+)- and (−)-enantiomers prepared separately, could then be administered separately or mixed together. If mixed together, the resulting solutions could be succussed or not succussed, and subsequently serially diluted or attenuated or potentised or not. Alternatively, the (+)- and (−)-enantiomers may not be prepared separately, and mixing could occur in the one container.

Also, in the spirit of the above description, 0.4 ml of $3^{rd}$ potency, attenuation, or dilution of the (−)-enantiomer, may be added to 1.2 ml of the $13^{th}$, 5.2 ml of the $41^{st}$, 4.5 ml of the $200^{th}$ and 3.7 ml of the 1000th potency, attenuation or dilution. This may then be succussed or not. In turn, this may then be added to a mixture of 5.1 ml of the $5^{th}$ potency, attenuation or dilution, 0.3 ml of the $37^{th}$, and 6.3 ml of the $105^{th}$ potency, attenuation or dilution of the (+)-enantiomer. This latter mixture may have been succussed or not. The resulting combination of mixtures may then be serially diluted, attenuated or potentised or not. In this paragraph the number denoting potencies, attenuations or dilutions can be replaced by any integers greater than zero. Numbers representing millilitres of potency, attenuation or dilution, can be replaced by any numbers greater than or equal to zero.

(+)- and (−)-enantiomers may be mixed 50:50 or 25:75 or in any proportion. Thus, a mixture could be prepared by adding 2 g of 4th, 12th and 30th potencies of (+)-enantiomer to 2 g of 4th, 12th and 30th potencies of (−)-enantiomer, or vice versa. Alternatively 0.5 g of 4th, 2 g of 12th and 3.4 g of 30th potencies could be used, and in fact the numbers 0.5, 2 and 3.4 could be replaced by any numbers greater than zero or equal to zero. Also, the 4th, 12th and 30th potencies could be replaced by any potencies represented by integers greater than or equal to 1. The mixtures of (+)- and (−)-enantiomers prepared separately, could then be administered separately or mixed together. If-mixed together, the resulting solutions could be succussed or not succussed, and subsequently serially diluted or attenuated or potentised or not. Alternatively, the (+)- and (−)-enantiomers may not be prepared separately, and mixing could occur in the one container.

Also, in the spirit of the above description, 0.4 ml of $3^{rd}$ potency, attenuation, or dilution of the (−)-enantiomer, may be added to 1.2 g of the $13^{th}$, 5.2 g of the $41^{st}$, 4.5 g of the $200^{th}$ and 3.7 g of the 1000th potency, attenuation or dilution. This may then be succussed or not. In turn, this may then be added to a mixture of 5.1 g of the $5^{th}$ potency, attenuation or dilution, 0.3 g of the $37^{th}$, and 6.3 g of the $105^{th}$ potency, attenuation or dilution of the (+)-enantiomer. This latter mixture may have been succussed or not. The resulting combination of mixtures may then be serially diluted, attenuated or potentised or not. In this paragraph the number denoting potencies, attenuations or dilutions can be replaced by any integers greater than zero. Numbers representing grams of potency, attenuation or dilution, can be replaced by any numbers greater than or equal to zero.

The same procedures as described above could be used for mixtures of diastereoisomers.

The administration of the potentised stereoisomer is typically by an oral route but may be administered intravenously, intramuscularly, transdermally, subcutaneously, intraperitoneally or via any mucous membrane (typically sublingually). It is particularly preferable to administer the potentised stereoisomer orally or sublingually. Specific examples of administration of the potentised stereoisomer include tablets, globuli, liquid dilutions for injection and liquid external preparations.

Another method of administering the potentised or attenuated stereoisomer is to use devices such as the MORA machine, Listen Machine or Vega Select Machine or other bioresonance or electrodermal testing devices to detect an electromagnetic or bioresonance signal from the potency or attenuation and then administer the signal in an unchanged, modified or inverted form to the organism to be treated. These devices which are commercially available, claim to be able to copy the effects of medicines, dilution or potency and pass the attributes of a medicine, dilution or potency onto a heretofore placebo or medicinally inactive vehicle. The terms "modification" or "inversion" of the signal includes changing the polarity of the signal.

In order to determine the appropriate potency of the stereoisomer in order to achieve the most effective treatment of the undesirable effect of the chemical agent it is usually preferred to commence by administering a low potency of the stereoisomer, say between 1 C-10 C inclusive (or 1×-10×) and gradually incrementally increasing the potency until the treatment is optimised. Experience may show that 6 C, 15 C, 30 C, 200 C are appropriate attenuations in most cases. Attenuation of 1000 C, 10,000 C or higher may also produce desirable results. This also applies for non-decimal and non-centesimal potencies.

The vehicles used to attenuate the stereoisomer may be selected from the group consisting of water, such as water for injection B.P. or U.S.P., lactose B.P. or U.S.P., sucrose B.P. or U.S.P. ethanol typically in suitable concentrations (e.g. 15-95%). Also absolute ethanol, purified water, glycerol 85% or other ethanol/water mixture may be used. Other vehicles will also be apparent to those skilled in the art of homoeopathy.

The methods of preparation of solid or liquid stereoisomers of chemical agents into potentised attenuations include where water-soluble or alcohol-soluble isomers are to be prepared into potencies the use of water B.P. or purified water alone, or in a mixture of water and ethanol, say, 30-45% ethanol. Ethanol-soluble stereoisomers may be prepared using higher concentration ethanol solutions, say 55-95% ethanol or absolute ethanol. It is possible to start using lower and incrementally lower ethanol concentrations as the potency reaches 3 to 5× or 3 to 5 C. Final homeopathic liquids often contain 30-40% ethanol. The stereoisomer may be prepared by a process of trituration. The process of trituration is particularly advantageous when the stereoisomer is not readily soluble in water, ethanol or water/ethanol mixes. At potencies beyond 3 C or 6× it is possible to convert from trituration to liquid dilutions or vice versa. For example, liquid dilutions may be prepared by first making a trituration and then diluting it in liquid such as water for injection.

In trituration one part of the medicinal substance, when preparing the first potency, or one part of the preceding attenuation when preparing the second or subsequent potencies, is added to one third of the total vehicle (e.g. lactose B.P.) used for that potency. The process of trituration is typically performed with mortar and pestle for 15 to 20 minutes. The side of the mortar is then scraped for five minutes to dislodge any attenuated substance with the pestle or with a spatula. Then the second third of the vehicle for attenuation is added to the mortar and the contents subjected to a further 15 to 20 minutes trituration prior to scraping the sides of the mortar for a further five minutes to dislodge attenuated substance. The remaining one third of the vehicle is added to the mortar and the combined mixture is subjected to trituration for a further 15 to 20 minutes to complete the trituration for that potency. Alternatively, the total vehicle may be added to the medicinal substance or preceding attenuation at each successive stage of potency preparation and subjected to 60 minutes of trituration. Each successive level of attenuation is called a potency.

The process of the present invention may be used to reverse, or in another embodiment enhance, the effects in vivo, and in vitro, of any optically active compounds. Another aspect of the invention provides for the use of the method of the present invention to enhance the effects in vivo and in vitro of any levorotatory compound or to reverse the effects in vivo and in vitro of any dextrorotatory compound.

Examples of chemical agents which exhibit effects which may be treated by the present process include a wide variety of physiologically active compounds such as pharmaceuticals, drugs of addiction, compounds naturally occurring in the organism and many others. The process of the present invention may be used to alleviate the side effects of pharmaceuticals, the addictive and undesirable effects of drugs of addiction, the toxicity of snake or other animal venoms or the toxic effects of stereoisomers contained in those venoms; e.g. cobrotoxin, batroxobin, or in general the toxic, physiological or pathological effects of any optically active molecules.

Included in the definition of chemical agents are those stereoisomers which undergo or have undergone in vivo transformation into a physiologically active form. For example, following absorption the drug enalapril is rapidly and extensively hydrolysed to enalaprilat, which is a potent angiotensin converting enzyme inhibitor. Another example is the prodrug atacand, which is rapidly converted to the active drug candesartan, an angiotensin 2 receptor antagonist by ester hydrolysis during absorption from the gastrointestinal tract. Dipivefrine hydrochloride is a prodrug which is transformed to liberate adrenaline, an adrenergic agonist into the anterior chamber of the eye.

Pharmaceuticals suitable for use in the present invention include propranolol. The most common form of propranolol used in medicine is (±)-propranolol hydrochloride (Inderal). This is a β-blocker mainly used for the treatment of hypertension or some cardiac arrhythmias. It is available in "dextro" (herein referred to as (+)) and "levo" (herein referred to as (−)) forms. (+)-propranolol is the inactive form, and has probably less than a hundredth the activity of racemic propranolol in blocking isoprenaline-induced tachycardia. In order to reduce the effects of the (−)-propranolol a potentised attenuation of (+)-propranolol may be used.

On the other hand (+)-propranolol and (±)-propranolol are equally effective in abolishing ouabain-induced arrhythmias, while (−)-propranolol has little effect. In order to reduce the effects of (+)-propranolol a potentised attenuation of (−)-propranolol may be used.

Other pharmaceuticals suitable for use in the present invention include tranylcypromine, deserpidine, trimipramine, mianserin, sertraline, paroxetine (and other selective serotonin re-uptake inhibitors), amoxycillin, cobrotoxin, batroxobin, flecainide, sotalol, simvastatin, pravastatin (and other HMG-CoA reductase inhibitors), prednisolone, prednisone, procyclidine, verapamil, (and other calcium channel blockers), capoten (and other angiotension converting enzyme inhibitors), haloperidol, melleril, digitoxin, digoxin, methotrexate (and other optically active cytotoxic or anti-neoplastic compounds), amantadine, cogentin, colchicine, naproxen (and other optically active non-steroidal anti-inflammatory compounds), warfarin, heparin, ethinyl estradiol, venlafaxine hydrochloride, fluoxetine hydrochloride, and sibutramine hydrochloride monohydrate.

The method of the present invention may also be used to treat the undesirable effects of drugs of addiction and the method of the present invention may also find use in the treatment of drug addiction or dependency, in particular for the reduction or alleviation of the physical and psychological effects of drug substances which are commonly abused. Examples of such drugs of addiction include amphetamines, opiates, cannabinoids, hallucinogens, cocaine and barbiturates. Specific examples of drugs of this kind include the following drugs and the salts thereof: morphine, codeine, heroin, phenazocine, Demerol, methadone, barbital, phenobarbital, amobarbital, pentobarbital, secobarbital, $\Delta^9$-Tetrahydrocannabinol, 11-Hydroxy-$\Delta^9$-tetrahydrocannabinol, amphetamine, methamphetamine, Lysergic Acid diethylamide (LSD), Scientifically Treated Petrol (STP), or any optically active component of modern "designer drugs". Where drugs exist in racemic mixtures, the physiological effects are counteracted (or enhanced) by administering a potentised attenuation of the enantiomer or less physiologically active or nonactive stereoisomer. The effects of nicotine addiction may be counteracted by preparing a potentised attenuation of a less active or nonactive enantiomer of the active isomer.

The method of the present invention may also be used to counter the effects of other physiologically active compounds including for example, optically active food additives such as monosodium glutamate or, environmental pollutants. (−)-adrenaline is the active form occurring in humans and by administering a potentised attenuation of (+)-adrenaline the tachycardic effects of (−)-adrenaline may be reversed. Similarly, (−)-amphetamine may be used to inhibit the effects of pharmaceutical doses of (+)-amphetamine such as insomnia or vice versa. Also, (+)-ephedrine may be used to inhibit the effects of pharmaceutical doses of (−)-ephedrine or vice versa.

Another aspect of the invention is the use of a dilution or an ultra-high dilution or potentised preparation of a stereoisomer of a chemical agent, which agent is characterised by one or more chiral centres for the preparation of a medicament for the treatment of a condition characterised by the effects of said chemical agent.

Another aspect of the invention is the use of a dilution or an ultra-high dilution or potentised preparation of a stereoisomer of a chemical agent, which agent is characterized by one or more chiral centres for the preparation of a medicament for the treatment of the toxic, physiological and/or pathological effects of said chemical agent.

Yet another aspect of the invention is the use of a dilution or an ultra-high dilution or potentised preparation of a stereoisomer of a chemical agent, which agent is characterized by one or more chiral centres for the preparation of a medicament for the alleviation of the side effects of pharmaceuticals.

Still yet another aspect of the invention is the use of a dilution or an ultra-high dilution or potentised preparation of a stereoisomer of a chemical agent, which agent is characterized by one or more chiral centres for the preparation of a medicament for the treatment of the addictive and other undesirable effects of drugs of addiction.

Still yet another aspect of the invention is the use of a dilution or an ultra-high dilution or potentised preparation of a stereoisomer of a chemical agent, which agent is characterized by one or more chiral centres for the preparation of a medicament for the alleviation of the physical and psychological effects of drugs of addiction.

Still yet another aspect of the invention is the use of a dilution or an ultra-high dilution or potentised preparation of a stereoisomer of a chemical agent, which agent is characterized by one or more chiral centres for the preparation of a medicament for the treatment of the toxic effects of animal venoms.

Another aspect of the invention is the use of a dilution or an ultra-high dilution or potentised preparation of a stereoisomer of a chemical agent, which agent is characterized by one or more chiral centres for the preparation of a medicament for the treatment of the toxic effects of snake venoms.

The present invention is further described by the following non-limiting examples.

Example 1

Homeopathic Treatment of Mice Administered Propanolol Hydrochloride

BALB/C mice are injected with the $LD_{50}$ of propranolol hydrochloride. This drug is a β-blocker which has been used to treat blood pressure and sometimes migraine. Students also use propranolol to decrease sweating and tremor in examinations where it actually promotes a relaxed feeling.

The $LD_{50}$ is the dose at which 50% of mice will die. The propranolol has the effect of slowing the heart rate with resultant unconsciousness and death. The $LD_{50}$ for mice is 565 mg/kg (orally), 22 mg/kg IV, and approximately 150 mg/kg intraperitoneally.

Half of the mice receive a homeopathic and the other half receive an indistinguishable placebo. Mice are analysed to determine if those in the treated group exhibit greater survival than those in the placebo group.

Example 2

Inhibition of (S)-(−)-Propranolol Hydrochloride by its Enantiomer in White Mice

Methods

This experiment insofar as the procedure of anaesthesia is concerned, was a modification of the procedure used for determining pentobarbitone sleeping time described by Lovell. Seventy-seven placebo ICR conventional mice and seventy-seven treatment group ICR conventional mice were utilized which gave the experiment an 80% power and test level of 5%. This assumed 64% survival in the treatment group and 40% survival in the placebo group. Equal numbers of male and female mice were allocated alternately to 2 groups called "A" and "B". A coin was then tossed to determine which of A or B would be the treatment group.

The following is a table of weight summary statistics.

Pilot Analysis with Weight

Summary Statistics of Weight (Grams)

| ARM | Mean | Std | N |
|---|---|---|---|
| 1 | 24.78 | 2.70 | 76 |
| 2 | 24.51 | 2.31 | 72 |
| All | 24.65 | 2.51 | 148 |

In the above table
1 = weight of medicine mouse and
2 = weight of placebo mouse.
All exclusions from the total sample were in accordance with prospective criteria.

To make the homeopathic potency for this experiment one hundred mg of (R)-(+)-propranolol HCl obtained from Fluka Chemie, Switzerland, ≧99% pure, was added to 5 ml 90% ethanol B.P. obtained from Sigma Chemical Company, Clayton, Victoria, Australia, in a brown tinted 20 ml glass bottle with dropper and rubber bulb, obtained from Plasdene Glaspak, Victoria, Australia. The bottle was closed and was given 20 forceful downward succussions by hand at the rate of ½-1 Hz. This was the first potency. Three drops from this bottle were added to a second identical bottle containing 9 ml of 90% ethanol B.P. (40 drops 90% ethanol was approximately 1 ml.) The second bottle was given 20 downward succussions at ½-1 Hz. This was the second potency. Three drops from the second potency were placed into a third bottle containing 9 ml ethanol and succussed as previously to produce the $3^{rd}$ potency and so on until the $29^{th}$ potency was produced. This was the potency used in the experiment. Therefore, the potentised propranolol used in this experiment was diluted by a factor of greater than $10^{52}$. This is well in excess of Avogadro's number ($6.023 \times 10^{23}$).

Indistinguishable placebo was prepared as above, but instead of 100 mg isomer being added to the first bottle, 3 drops of 90% ethanol were added to a bottle containing 5 ml 90% ethanol B.P. The 90% ethanol used for preparation of placebo came from the same bottle of ethanol, which was used for preparation of the homeopathic medicine. Subsequent "potencies" of placebo were succussed as described above for the isomer potencies until the $29^{th}$ potency of placebo was prepared. This was the indistinguishable placebo, which was used in the experiment.

ICR Mice were bred in a standard non-pathogen free animal house and transferred to the laboratory animal house (temperature 20-22° C., photoperiod 7 am to 7 pm, 1 week before the experiment to allow acclimatization. During breeding mice were fed their standard diet. The inventor's preference was to use non-irradiated Mouse Maintenance Diet (RM1 expanded) (Special Diets Services Ltd). During breeding mice were fed non-irradiated Mouse Maintenance Diet (RM3 expanded). However, due to non-availability of this product a standard mouse diet for mice available at the Institute of Zoology was used. The only investigator blinded during this experiment was the anesthetist. This was considered to be the most likely step in the experiment at which bias could be introduced.

At 4.30 pm on the day before the experiment, mice were given treatment and placebo fluids using disposable non-heparinized hematocrit capillary tubes (75 mm/75 microlitre, Hirschmann Laborgeräte). For this purpose a mouse was taken from its cage by an experienced mouse handler and held in a supine position. Using a hematocrit tube, this person removed approximately 0.05 ml of the respective medicine or placebo from the storage test tubes (containing medicine or placebo). The filled hematocrit tube was introduced just behind the incisors of the mouse such that it was impelled to drink quickly. The tube was removed as soon as possible and the mouse was held for another 20 seconds in the supine position. Each mouse was then returned to its cage. Mice in fact seemed keen to drink both treatment and placebo fluids and generally the hematocrit tube just needed to be presented close to the incisors, and the mice then drank readily from them.

Each cage had a constant amount of unautoclaved softwood (pine) bedding just covering the cage floor. Cages were made out of plastic with a wire see-through roof. The drinking water bottle and food was not placed in the cage until 10 minutes later. This same procedure was repeated between 9.00-9.30 am on the morning of the experiment, with the exception that prior to giving each mouse it's respective medicine or placebo, the mouse was placed in a clean strong plastic bag and suspended from a Pesola 30 g or 60 g scale (Pesola, Switzerland, www.pesola.ch), to measure weight in grams. Mice were allowed food and water ad libitum at all stages of the experiment up until just before the injection of anaesthetic, with the exception of the brief period of abstinence (10 minutes) after giving oral liquids by capillary pipette.

To prepare the homeopathy used each day in the experiment, 5 drops of the $29^{th}$ potency prepared as described above were added to 15 mls of water in a 20 ml Hamilton Laboratory Glass test tube with a glass stopper. The test tube was not filled more that two-thirds with liquid. The test tube was given 20 forceful downward succussions or shakes. Black paper was placed around the test tube to protect it from light. The placebo specimen was prepared in the same way. All glassware such as test tubes used recurrently during the experiment was washed with tap water, copiously rinsed with distilled water, hot-air dried and finally heated for 2 hours at 200° C. before being considered clean and reusable (Blackie Foundation Trust). The same glassware was used for treatment and placebo preparation. In addition, (see Kuzeff et al (reference 12) and Kuzeff et al (2) (reference 13), cages and water bottles were washed after each experiment with "Pur+Aloe Vera" (pH neutral, Henkel, Austria, 245604), mixed 50:50 with Belina ACE (Greece). Both these products are commercially available in Sofia.

Between 12 and 16 mice were selected each afternoon about 4.30 pm. They were divided into two groups of 6-8 and each group was placed in a plastic cage approximately 24 cm×14.5 cm with walls 14 cm high, with stainless steel mesh roof, cradle for inserting a water bottle, and grill onto which could be placed dry food for ad libitum consumption. At the start of the experiment only 12 mice were tested each day. As the experimenters became accustomed to the procedure this number was increased to 16. Mice were administered potency or placebo according to the method described in the next paragraph, which relates the conduct of the experiment on the morning of the next day.

The experiment started when a mouse was removed from its cage between 10-11 am in the morning, and held gently but firmly in the supine position. It was injected i.p. (intraperitoneal) with a solution of 2% Xylazine hydrochloride (Rometar, Spofa, Prague) diluted 50:50 in Normal saline B.P. for injection. The volume of this solution administered to mice intraperitoneally was 0.1 ml/10 gm body weight. Injections were given using a 0.5 ml Becton-Dickinson insulin syringe with 27 gauge needle, intraperitoneally into the left lower quadrant of the mouse's abdomen by an experienced anaesthetist. After injection the mice were held in the supine position for approximately 2-5 minutes until asleep or heavily sedated. Each mouse was then placed into an individual plastic mouse cage with softwood bedding but no lid. They remained here until the process of administration of oral potency or placebo was finished. After this they were returned to their communal group A or group B cage which had ad libitum food and water available. The number of mice alive at 9 am the next morning was the end point of the experiment.

S-(−)-Propranolol HCl was dissolved in sufficient Normal Saline B.P. such that injecting 0.1 ml/10 gm body weight of the solution intraperitoneally would give a dose of isomer of 155 mg/kg. The S-(−)-propranolol diluted in Normal Saline for Injection B.P. in this manner is not very soluble. Dissolution was assisted by placing the 10 ml Hamilton Laboratory Glassware test tube containing the Normal Saline and (S)-(−)-Propranolol HCl into a beaker containing warm tap water at approximately 40° C.

Treatment and placebo mice were alternately presented in random order to the anaesthetist who was blinded to the sequencing. This means that on some of the days of the experiment a placebo mouse was presented first for Rometar injection and on other days it was a treatment mouse. This was done for both Rometar and (S)-(−)-propranolol injections.

Five minutes after injection of Rometar the mice were heavily sedated or asleep. It was at this point that treatment and placebo mice were injected with (S)-(−)-propranolol HCl in alternate sequence, in the same order in which they were injected with Rometar. After all mice had received i.p. (S)-(−)-propranolol HCl, they were administered oral treatment or placebo in the same sequence in which they had received their injections. According to the protocol each mouse was then to be given 1 drop of potentised isomer or placebo, at approximately 5, 10, 15, and 20 minutes after (S)-(−)-propranolol HCl injection, and also at 30, 40, 50, 80 and 110 minutes.

Results

It should be noted that the dose of (S)-(−)-propranolol HCl injected in this experiment was started at 107 mg/kg intraperitoneally and by trial and error on successive days it was determined that the LD50 of (S)-(−)-propranolol HCl i.p. was approximately 155 mg/kg. In the course of the experiment batches of mice were at various times also injected with 214 mg/kg i.p. and 180 mg/kg i.p.

The trend for survival was in favour of homeopathy with somewhere between 9% and 24% more mice surviving than placebo mice. Mouse recovery was substantially faster in the treatment mice than in the placebo mice.

Example 3

Inhibition of (S)-(−)-Propranolol Hydrochloride by its Enantiomer in White Mice (2)

Methods

ICR conventional mice were used in this experiment. The experiment was performed between December 2001 and April 2002 using 3 batches of mice. 254 placebo mice and 254 treatment group mice were used in this experiment. The following is a table of weight summary statistics.

Double-Blind Analysis with Weight

Summary Statistics of Weight (Grams)

| ARM | Mean | Std | N |
| --- | --- | --- | --- |
| m | 23.20 | 3.99 | 238 |
| p | 23.48 | 4.55 | 246 |
| All | 23.34 | 4.29 | 484 |

In the above table
m = weight of medicine mouse and
p = weight of placebo mouse.
All exclusions from the total sample were in accordance with prospective criteria.

Placebo mice mean was 23.50 gm SD=4.51, n=254. As discussed in Example 2, assuming that the real difference in survival was somewhere between 9% and 24%, a sample of approximately 500 mice, 250 treatment and 250 placebo, assuming p=0.05 with 17% improved survival in the treatment group, i.e., 50% survival in the treatment group and 33% survival in the placebo group, gives a power of 0.95 for a two-sided test, and 0.98 for a one-sided test (Hennekens et al (1987)).

Homeopathy was prepared fresh every 2 days as follows. Twenty mg (R)-(+)-propranolol hydrochloride, obtained from Fluka Chemie, Switzerland, ≧99.9% pure, was added to two mls 40% ethanol B.P. in a 10 ml Hamilton Laboratory Glass test tube with a glass stopper (Hamilton Laboratory Glass Ltd). This is neutral glass type one in the European Pharmacopoea. Twenty forceful downward succussions were given to the fluid in the test tube, in a vertical line at a rate of between one-two Hertz. A non-heparinised disposable hematocrit capillary tube (75 mm/75 microlitre, Hirschmann Laborgeräte) was used to add 3 drops of this solution to another test tube containing 7 ml 40% ethanol B.P.—ten ml Hamilton Laboratory Glass test tubes were again used (40 drops, 40% ethanol, approximately=1 ml).

Note that the test tube should not be more than two-thirds full, i.e., there must be plenty of room in the test tube for the fluid to collide violently with the test tube walls when it is succussed. This second test tube was succussed 20 times at one-two Hertz. Three drops of this potency were added to a third 10 ml Hamilton test tube containing once again 7 ml 40% ethanol B.P. The same process was repeated until the $29^{th}$ dilution or potency was reached. The $30^{th}$ potency was prepared from the $29^{th}$ in the same manner. The $29^{th}$ potency was stored in a dark place and wrapped in paper for use the next day. A fresh $29^{th}$ potency was prepared every 2 days.

Indistinguishable placebo was prepared by adding 3 drops from a hematocrit capillary tube to a 10 ml test tube containing 7 ml 40% ethanol B.P. and giving 20 succussions as above described for the medicine preparation. All glassware such as test tubes used recurrently during the experiment was washed with tap water, copiously rinsed with distilled water, hot air dried and finally heated for 2 hours at 200° C. before being considered clean and reusable (Blackie Foundation Trust). The same glassware was used for treatment and placebo preparation. In addition, (see Kuzeffet al (reference 12) and Kuzeffet al (2) (reference 131 cages and water bottles were washed after each experiment with "Pur+Aloe Vera" (pH neutral, Henkel, Austria, 245604), mixed 50:50 with Belina ACE (Greece). Both these products are commercially available in Sofia.

It should be noted that 40% ethanol produces a type of froth when succussed in this way. The rate of succussion was performed to be sufficiently slow to enable this froth to settle down substantially between each individual succussion. The indistinguishable placebo consisted of 7 ml 40% ethanol B.P. added to an indistinguishable Hamilton Laboratory Glass test tube. This was given 20 succussions as above described for the medicine preparation.

Prior to the commencement of the experiment at 9.30 am each day, an individual who did not participate in the actual conduct of the experimental protocol, other than performing randomisation, took the indistinguishable test tubes containing potency and placebo into a closed room. One sticky label was marked with the letter "A" and another sticky label was marked with the letter "B". A coin was tossed to determine if A or B would correspond to medicine or placebo. The test tube containing potency was wrapped with paper and labeled with the sticker, "A" or "B", indicated by randomization. The placebo-containing test tube was wrapped with indistinguishable paper in the same way as the potency-containing test tube, and again the appropriate label was affixed according to randomisation. The blind randomization code was kept in the personal possession of the randomiser until after the experiment and not revealed to any other person.

Mice were bred in a standard animal house and transferred to the laboratory animal house (temperature 20-22° C., photoperiod 7 am to 7 pm, 1 week before the experiment to allow acclimatization. During breeding mice were fed their standard diet. In the past this had been non-irradiated Mouse Maintenance Diet (RM1 expanded) (Special Diets Services Ltd). During breeding mice were fed non-irradiated Mouse Maintenance Diet (RM3 expanded) (Walker et al, 1993). However, due to non-availability of this product, a standard mouse diet available at the Institute of Zoology was used.

Treatment and placebo fluids were given to mice using disposable hematocrit capillary tubes referred to (75 mm/75 microlitre, Hirschmann Laborgeräte). For this purpose a mouse was taken from its cage by an experienced mouse handler and held in a supine position. This person removed approximately 0.05 ml of the respective blinded and randomised medicine or placebo from the storage test tubes (containing medicine or placebo). The filled hematocrit tube was introduced just behind the incisors of the mouse such that it was impelled to drink quickly. The pipette was removed as soon as possible and the mouse was held for another 20 seconds in the supine position. Each mouse was then returned to its cage.

Each cage had a constant amount of unautoclaved softwood (pine) bedding just covering the cage floor. Cages were made out of plastic with a wire see-through roof. The drinking water bottle and food were not placed in the cage until 10 minutes later. This same procedure was repeated between 9.00-9.30 am on the morning of the experiment, with the exception that prior to giving each mouse it's respective medicine or placebo, the mouse was placed in a clean strong plastic bag and suspended from a Pesola 30 g or 60 g scale (Pesola, Switzerland, www.pesola.ch), to measure weight in grams. Mice were allowed food and water ad libitum at all stages of the experiment up until just before the injection of anaesthetic, with the exception of the brief period of abstinence (10 minutes) after giving oral liquids by capillary tube.

Sixteen mice were selected each afternoon about 4.30 pm. They were divided into two groups of 8 and each group was placed in a plastic cage approximately 20 cm×30 cm with walls 20 cm high, with wire mesh see-through roof, cradle for inserting a water bottle, and grill onto which could be placed dry food. A coin was tossed to determine which group would be called "group A", and the other group was called "group B". A coin was tossed again (unnecessarily since test tubes A and B were already randomised), to determine if group A mice would be allocated to receive test tube A or test tube B in the experiment. Group B mice then received the opposite. Mice were then given randomised and blinded potency or placebo as described in the paragraph below which relates the conduct of the experiment on the morning of the following day.

Two investigators and two laboratory assistants were involved in the performance of the experiment and a third investigator performed randomisation and blinding only. The four mouse handlers were divided into two groups of two handlers for the experiment on each day. This was done by placing the numbers 1-4 on each of 4 identical cards which were place in a box which was shaken. The cards were then withdrawn blind by each investigator. Investigators who in this way selected the numbers one or two were paired for the experiment and handled the "group A" of mice. Those who extracted numbers 3 and 4 handled the "group B" of mice on a given day of the experiment. This was an extra precaution to decrease the risk of systematic biases being introduced in the handling of the animals, although strictly speaking it was not necessary in a randomised and blinded experiment. The experiment started when a mouse was removed from its cage between 10-11 am in the morning, and held gently but firmly in the supine position. It was injected i.p. with a solution of 2% xylazine hydrochloride (Rometar, Spofa, Prague) diluted 50:50 in physiological saline for injection B.P. The volume of this solution administered to mice intraperitoneally was 0.1 ml/10 gm body weight. Injections were given using a 0.5 ml insulin syringe with 27 gauge needle, intraperitoneally into the left lower quadrant of the mouse's abdomen by an experienced anaesthetist. After injection the mice were held in the supine position for approximately 2-5 minutes until asleep or heavily sedated. Each mouse was then placed into an individual plastic mouse cage with softwood bedding but no lid. They remained here until the process of administration of oral potency or placebo was finished. After this they were returned to their communal group A or group B cage which had ad libitum food and water available. The number of mice alive at 9 am the next morning was the end point of the experiment. It was estimated that under the conditions of this experiment the LD50 of (S)-(−)-propranolol hydrochloride injected intraperitoneally into white ICR mice was approximately 155 mg/kg. This was determined over a few days by trial and error starting at a dose of 107 mg/kg i.p. as suggested elsewhere.

(S)-(−)-Propranolol HCl was dissolved in sufficient Normal Saline B.P. such that injecting 0.1 ml/10 gm body weight of the solution would give a dose of isomer of 155 mg/kg. Treatment and placebo mice were alternately presented to the anaesthetist. The (S)-(−)-Propanolol diluted in Normal Saline for Injection B.P. in this manner is not very soluble. Dissolution was assisted by placing the 10 ml Hamilton Laboratory Glassware test tube containing the Normal Saline and (S)-(−)-Propanolol HC into a beaker containing warm tap water at approximately 40° C.

Five minutes after injection of Rometar the mice were heavily sedated or asleep. It was at this point that the mice were injected with (S)-(−)-propranolol HCl in alternate sequence, in the same order in which they were injected with Rometar. Mice which died prior to injection of (S)-(−)-propranolol were excluded according to the prospective design. After all mice had received i.p. (S)-(−)-propranolol HCl, they were administered oral treatment or placebo in the same sequence in which they had received their injections. Each mouse was given 1 drop of potentised isomer or placebo, according to randomisation and blinding, at approximately 5, 10, 15, and 20 minutes after (S)-(−)-propranolol HCl injection, and also at 30, 40, 50, 80 and 110 minutes.

Results

It should be noted that the dose of (S)-(−)-propranolol HCl injected in this experiment was started at 130 mg/kg intraperitoneally. Over the ensuing 6 months we attempted to maintain with varying success approximately 50% mortality in the treatment mice. Doses of 130 140 and 155 microgram/kg were injected intraperitoneally. The LD50 for the mice seemed to vary somewhat perhaps depending on season and the weight and age of the batches of mice which were being tested. As already mentioned this experiment was performed in 3 batches between 86 to 240 mice. Note that in the analysis "medicine" refers to dose of intraperitoneal (S)-(−)-propranolol hydrochloride which was injected and not to the homeopathic medicine which was potenitized (R)-(+)-propranolol hydrochloride. The homeopathic medicine is referred to as "treatment".

The end-point for statistical analysis was the difference in survival between the placebo and treatment mice at 9 am on the morning after they were injected. 254 treatment and 254 placebo mice were admitted to the experiment. Twenty-four mice in total died after injection of intraperitoneal rometar and before injection of intraperitoneal isomer—sixteen treatment mice and eight placebo mice. The exclusion of these mice was in accordance with prospective criteria. Prospectively it was anticipated to perform a Chi-square test on the entire body of randomised data, but a logistic regression analysis was also done, to take into account weight of mice and dosage of intraperitoneal (S)-(−)-propranolol hydrochloride which was injected. Statistical analysis was performed by Statistical Investigations Pty Ltd., and a summary of the analysis follows as it was presented by the statistical consultant:

Chi-Square Tests
Cross-Tabulation of 'Arm' vs 'a_d':

TABLE 1

|  | Alive | Dead | Odds | OR |
|---|---|---|---|---|
| Medicine | 117 | 121 | 0.97 | 1.52 |
| Placebo | 96 | 150 | 0.64 | 1 |
| Total | 213 | 271 |  |  |

Under the null hypothesis that:
the proportions of alive and dead are the same for medicine and placebo
the Chi-Square=5.0429 with 1 degree of freedom, which has a probability of 0.0247. So we reject the null hypothesis at the 0.05 significance level.

Logistic Models

Logistic regression models were used to express the relationship between a dichotomous outcome (alive/dead) and the experimental factors: 'arm' (medicine/placebo), '(−)-prop' (dose of (−)-propranolol hydrochloride injected i.p. in mg/kg), and weight category (Low, Medium, or High). The weight categories are defined by the 33.3 percentile (21.5 g) and 66.7 percentile (24.0), i.e. Low: $\leq 21.5$ g, Medium: 21.6 g-24.0 g and High: $\geq 24.1$ g.

A series of models were fitted starting with a saturated model. Subsequent steps in the search for the best model involved fitting additional models that represented the successive removal of terms from the saturated model. At each step a statistical test ('likelihood ratio test') was carried out to see if there was a statistically significant difference between the models. The process was stopped when there was a significant difference between models, because this indicated that the last term that was removed significantly reduced the fit of the model.

The result of this model fitting process is a model that can be summarised as follows (degrees of freedom in brackets):

Log of the odds of survival=intercept(1)+arm(1)+ treatment(2)+weight(2)+weight*treatment(4)

Parameter estimates for this model are:

TABLE 5

| Parameter | DF | Estimate | Standard Error | Chi-Square | Pr > ChiSq |
|---|---|---|---|---|---|
| Intercept | 1 | −0.0240 | 0.1127 | 0.0454 | 0.8313 |
| ARM (medicine) | 1 | 0.2072 | 0.0945 | 4.8112 | 0.0283 |
| (-)-prop (130 mg/kg) | 1 | 0.1438 | 0.1490 | 0.9313 | 0.3345 |
| (-)-prop (140 mg/kg) | 1 | 0.0654 | 0.1792 | 0.1333 | 0.7150 |
| Weight (Low) | 1 | −0.0515 | 0.1486 | 0.1200 | 0.7290 |

TABLE 5-continued

| Parameter | DF | Estimate | Standard Error | Chi-Square | Pr > ChiSq |
|---|---|---|---|---|---|
| Weight (Medium) | 1 | −0.2445 | 0.1485 | 2.7096 | 0.0997 |
| (-)-prop (130 mg/kg) by Weight (Low) | 1 | −0.0833 | 0.1961 | 0.1806 | 0.6709 |
| (-)-prop (130 mg/kg) by Weight (Medium) | 1 | −0.1760 | 0.1969 | 0.7985 | 0.3715 |
| (-)-prop (140 mg/kg) by Weight (Low) | 1 | −0.5236 | 0.2187 | 5.7315 | 0.0167 |
| (-)-prop (140 mg/kg) by Weight (Medium) | 1 | −0.0340 | 0.2325 | 0.0214 | 0.8837 |

(-)-prop = dose of (-)-propranolol HCL injected intraperitoneally in mg/kg

Under the null hypothesis (parameter=0) the square of ratio of the parameter estimate to its standard error has a Chi-Square distribution (I degree of freedom). In the above table the 'ARM (medicine)' factor and '(−)-prop (140 mg/kg) by Weight (Low)' interaction have P-values less than 0.05, thus in both cases we reject the null hypothesis of zero parameter value.

As there is a weight by i.p. (−)-propranolol interaction in this model, an odds ratio can only be calculated for the arm factor. It is 1.51 with a 95% CI of for 1.045 to 2.19. This odds ratio estimate shows that the treatment mice were 1.5 times more likely to survive than placebo mice.

The end-point for statistical analysis was the difference in survival between the placebo and treatment mice. The odds ratio estimates show that the treatment mice were 1.5 times more likely to survive than placebo mice. This was statistically significant with p=0.025 with Chi Square test and 0.028 using the logistic regression model. Eleven percent more treatment mice survived than placebo mice.

Example 4

Inhibition of (−)-Trans-(1S,2S)-U-50488 by its Enantiomer in White Mice

A Blind Randomised Placebo-Controlled Study

Homeopathy was prepared as follows. Ten mg (+)-trans-(1R,2R)-U-50488 was added to one ml distilled water in a 10 ml Hamilton Laboratory Glass test tube with a glass stopper (Hamilton Laboratory Glass Ltd). This is neutral glass type one in the European Pharmacopoeia. Twenty forceful downward succussions were given to the fluid in the test tube, in a vertical line at a rate of between one-two Hertz. A non-heparinised disposable 40 drops in 1 ml hematocrit capillary tube (75 mm/75 microlitre, Hirschmann Laborgeräte) was used to add 3 drops of this solution to another test tube containing 7 ml 40% ethanol B.P. Ten ml Hamilton Laboratory Glass test tubes were used again (40 drops 40% ethanol approximately =1 ml).

The test tube was not more than two-thirds full, i.e., there must be plenty of room in the test tube for the fluid to collide violently with the test tube walls when it is succussed. This second test tube was succussed 20 times at one-two Hertz. Three drops of this potency was added to a third 10 ml Hamilton test tube containing once again 7 ml 40% ethanol B.P. The same process was repeated until the $29^{th}$ dilution or potency was reached. The $30^{th}$ potency was prepared from the $29^{th}$ in the same manner. Potencies were stored in a dark place and wrapped in paper for use on later days. They were stored in the dark away from direct sun and sources of electromagnetic energy such as power cables, computers, television, metal surfaces, refrigerators and other electrical equipment. The potencies were not stored near substances with strong smells. Indistinguishable placebo was prepared by adding 3 drops of 40% ethanol from a hematocrit capillary tube to a 10 ml test tube containing 7 ml 40% ethanol BP and giving 20 succussions as per the treatment preparation. All glassware such as test tubes used recurrently during the experiment was washed with tap water, copiously rinsed with distilled water, hot air dried and finally heated for 2 hours at 200° C. before being considered clean and reusable (Blackie Foundation Trust). The same glassware was used for treatment and placebo preparation. In addition, (see Kuzeff et al and Kuzeff et al (2), cages and water bottles were washed after each experiment with "Pur+Aloe Vera" (pH neutral, Henkel, Austria, 245604), mixed 50:50 with Belina ACE (Greece). Both these products are commercially available in Sofia.

Homeopathy for use in this experiment was prepared as follows: 1.5 ml of liquid was removed from the tube with the $4^{th}$ potency and added to a 10 ml Hamilton Laboratory test tube. Likewise 1.5 ml was removed from the $12^{th}$ potency and added to the same tube. Then 1.5 ml was removed from the $30^{th}$ potency and added to the tube. The contents were given 20 forceful downward succussions at 1-2 Hertz to prepare the potency H1. This is the mixture, which was used in the experiments. It is important that the mixture of the $4^{th}$, $12^{th}$ and $30^{th}$ potencies occurs quickly, eg. within 30 seconds, so that the tube can be given succussions quickly.

To make the potency for use in the experiment 3 drops of H1 is added to a test tube containing 7 ml 40% ethanol. This is immediately given 20 succussions at 1-2 Hz to produce H2. The test tube was then wrapped with white paper. This is the final preparation which was administered to the mice.

Placebo Preparation

The placebo was made immediately before the medicine every morning. This was done to try to avoid contamination of the placebo with the potency. The indistinguishable placebo was made by adding 3 drops of 40% ethanol from a capillary hematocrit tube to a test tube containing 7 ml 40% ethanol B.P. added to an indistinguishable Hamilton Laboratory Glass test tube. This was given 20 succussions as above described for the medicine preparation. This was made fresh daily. The test tube was then wrapped with white paper.

It should be noted that 40% ethanol produces froth when succussed in this way. The rate of succussion was performed to be sufficiently slow to enable this froth to settle down substantially between each individual succussion.

Before the start of the experiment at 9:30 am each day, an individual who did not participate in the conduct of the experimental protocol, other than performing randomisation, took the indistinguishable test tubes into a closed room. The placebo was made first every morning and after that the potency. This was to avoid contamination of the placebo. Stickers were available named "A" and "B". After the placebo was made a coin was tossed to decide if the medicine or placebo was going to be called "A" or "B". The placebo was then wrapped with paper with the sticker "A" or "B" stuck onto it according to the randomisation. The potency or medicine-containing test tube was wrapped with indistinguishable paper in the same way as the placebo-containing test tube and again the appropriate label was affixed according to randomisation. The blind randomisation code was kept in the personal possession of the randomiser until after the experiment and not revealed to any other person.

Mice were bred in a standard animal house and transferred to the laboratory animal house (temperature 20-22° C., photoperiod 7 am to 7 pm, 1 week before the experiment to allow. During breeding mice were fed their standard diet. This consisted of a standard mouse diet available at the Institute of Zoology.

Treatment and placebo fluids were given to mice using the disposable hematocrit capillary tubes. (This was done after selecting the new groups of mice at 4.30 pm each day and also at about 9.30 am the next morning. To give oral fluids a mouse was taken from its cage by an experienced mouse handler and held in a supine position. This person removed approximately 0.05 ml of the respective blinded and randomised medicine or placebo from the storage test tubes (containing medicine or placebo). The filled hematocrit tube was introduced just behind the incisors of the mouse such that it was impelled to drink quickly. The pipette was removed as soon as possible and the mouse was held for another 20 seconds in the supine position. Each mouse was then returned to its cage. The drinking water bottle and food were not placed in the cage until 10 minutes later. This same procedure was repeated between 9.00-9.30 am on the morning of the experiment, with the exception that prior to giving each mouse its respective medicine or placebo, the mouse was placed in a clean strong plastic bag and suspended from a Pesola 30 g or 60 g scale (Pesola, Switzerland, www.pesola.ch), to measure weight in grams. Mice were allowed food and water ad libitum at all stages of the experiment up until just before the injection of anaesthetic, with the exception of the brief period of abstinence (10 minutes) after giving oral liquids by capillary tube.

Each cage had a constant amount of unautoclaved softwood (pine) bedding just covering the cage floor.

Mouse Selection

Eighteen mice were selected each afternoon about 4.30 pm except day one when 16 were selected. All mice were placed in one cage. A mouse was removed from this cage and a coin was tossed to decide randomisation to group "A" or group "B". As soon as 9 mice were in either group "A" or group "B", then the remaining mice of the eighteen selected were allocated to the group which did not contain 9 mice yet. The group of 16 on day one was treated analogously. Group "A" and group "B" mice were housed in a plastic cage approximately 24 cm×14.5 cm with walls 14 cm high, with stainless steel mesh roof, cradle for inserting a water bottle, and grill onto which could be placed dry food.

A coin was tossed again to determine if group A mice would be allocated to receive test tube A or test tube B in the study. Group B mice then received the opposite.

Two investigators and two laboratory assistants were involved in the performance of the study and a third investigator performed randomisation and blinding only. The four mouse handlers were divided into two groups of two handlers for the experiment on each day. This was done by placing the numbers 1-4 on each of 4 identical cards, which were placed in a box, which was shaken. Each investigator then withdrew the cards blind. Investigators who in this way select the numbers one or two were paired for the experiment and handled "group A" mice. Those who extracted numbers 3 and 4 handled the "group B" mice on a given day of the experiment.

The next part of the experiment started when a mouse was removed from its cage between 10-11 am in the morning, and held gently but firmly in the supine position. It was injected i.p. with a solution (−)-U50488 diluted in normal saline for injection B.P. During the first 3 days 52 mice of the total 210 were used to estimate the LD50 of (−)-U50488 which is approximately 25 mg/kg i.p. This left 158 mice available for analysis. The volume of this solution administered to mice intraperitoneally was 0.1 ml/10 gm body weight. Injections were given using a 0.5 ml insulin syringe with 27-gauge needle, intraperitoneally into the left lower quadrant of the abdomen by an experienced anaesthetist. After injection the mice were held in the supine position for approximately 2-5 minutes until asleep or heavily sedated. Each mouse was then placed into an individual plastic mouse cage with softwood bedding but no lid. They remained there until the process of administration of oral potency or placebo was finished. After this they were returned to their communal group A or group B cage, which had ad libitum food and water available. The number of mice alive at 9 am the next morning was the end point of the experiment.

After all mice had received i.p. (−)-trans-(1S,2S)-U-50488, they were given oral treatment or placebo in the same sequence in which they had received their injections. Each mouse was given 1 drop of potentised isomer or placebo orally by capillary hematocrit tube, according to randomization and blinding, at approximately 5, 10, 15, and 20 minutes after (−)-U50488 injection, and also at 30, 40, 50, 80 and 110 minutes.

Results

Approximately 19.5% more treatment mice survived than placebo mice after administration of the LD50.

Cross-Tabulations

The body weight categories are defined by the 33.3 percentile (22.5 g) and 66.7 percentile (25.0), i.e. Low: ≦21.5 g, Medium: 21.6 g-24.0 g and High: ≧24.1 g.

It can be seen in the following cross-tabulations that some of the cells have low or zero frequencies.

TABLE 1

Table 1 of i.p.U50488 by BodyWeight
Controlling for ARM = homeop

| IPU50488 | BodyWeight | | | |
| | LO | MED | HI | Total |
|---|---|---|---|---|
| 10 | 2 | 2 | 4 | 8 |
| 20 | 1 | 3 | 14 | 18 |
| 25 | 36 | 22 | 21 | 79 |
| Total | 39 | 27 | 39 | 105 |

TABLE 2

Table 2 of IPU50488 by BodyWeight
Controlling for ARM = placebo

| IPU50488 | BodyWeight | | | |
| | LO | MED | HI | Total |
|---|---|---|---|---|
| 10 | 0 | 4 | 4 | 8 |
| 20 | 3 | 8 | 7 | 18 |
| 25 | 31 | 30 | 17 | 78 |
| Total | 34 | 42 | 28 | 104 |

These low frequency cells stop the estimation method used in logistic regression (method of maximum likelihood) from converging. This in turn leads to highly imprecise and biased estimates. In order to get convergent parameter estimates the following logistic model is fitted only to i.p U50488=25 mg/kg, only. This was the estimated LD50 and is in accordance with the prospective study design.

Logistic Models

Logistic regression models were used to express the relationship between a dichotomous outcome (alive/dead) and the experimental factors: 'arm' (medicine/placebo), and body weight category (Low, Medium, or High).

Two models were fitted. The first contained an interaction between body weight and arm and represents the saturated model (as many parameter estimates as unique cells in the data). The next model had the interaction term removed.

A statistical test ('likelihood ratio test') was carried out to see if there was a statistically significant difference between the models. There was no significant difference between the models (i.e. the interaction term was not significant), so the second model was adopted (degrees of freedom in brackets):

Log of the odds of survival=intercept(1)+arm(1)++
bodyweight(2)

Parameter estimates for this model are:

| Parameter | | DF | Estimate | Standard Error | Chi-Square | Pr > ChiSq |
|---|---|---|---|---|---|---|
| Intercept | | 1 | 0.3624 | 0.1722 | 4.4267 | 0.0354 |
| ARM | homeop | 1 | 0.4167 | 0.1673 | 6.2030 | 0.0128 |
| Body Weight | LO | 1 | −0.3009 | 0.2254 | 1.7816 | 0.1820 |
| Body Weight | MED | 1 | 0.0267 | 0.2402 | 0.0124 | 0.9114 |

Under the null hypothesis (parameter=0) the square of ratio of the parameter estimate to its standard error has a Chi-Square distribution (1 degree of freedom). In the above table the 'ARM (homeop)' factor has a P-values less than 0.05, thus we reject the null hypothesis of zero parameter value.

| | Odds Ratio Estimates | |
|---|---|---|
| Effect | Point Estimate | 95% Wald Confidence Limits |
| ARM homeop vs placebo | 2.301 | 1.194   4.434 |
| BodyWeight LO vs HI | 0.563 | 0.243   1.305 |
| BodyWeight MED vs HI | 0.781 | 0.322   1.896 |

As the estimate of 'ARM (homeop)' is significantly different from zero, its odds ratio has a 95% confidence interval that does not contain 1.

Discussion

Statistical analysis was the same as previously performed for the Examples 2 and 3. The end point for statistical analysis was the difference in survival between the placebo and treatment mice. The odds ratio for survival of treatment mice relative to placebo mice was 2.301. The analysis was adjusted for mouse weight using a logistic regression (LR) model. The LR treatment odds ratio for survival of treatment mice relative to placebo mice was 2.301 and the LR treatment Chi-Square was 6.2030 (1 degree of freedom), which has a P-value of 0.0128. In this study we confirm that toxicity of (−)-U50488 can be counteracted by administration of an attenuation, and in this case a potentised preparation of its enantiomer.

Therefore the study confirms the hypothesised method whereby the toxicity of an optically active molecule may be decreased by administration of its enantiomer. Although it was prospectively hoped to first of all determine the LD50 and then subsequently do the experiment using 500 mice, this was not possible because there was only sufficient (−)-U50488 for 210 mice. Of these the first 52 mice were used to establish an approximate LD50 of 25 mg/kg. Inclusion of the first 52 mice transgressed the assumptions of the subsequent prospectively selected logistic regression model and these were excluded from the analysis. One mouse in the placebo group was excluded because it died immediately after i.p. injection of (−)-U50488.

Example 5

(+)-ephedrine hydrochloride and (−)-ephedrine hydrochloride are utilised to modulate the locomotor activity. One isomer could be counteracted by administration of a potentised solution of its enantiomer. This is done by adapting the methodology described by Walker, R. B., Fitz, D. Williams, L. M. The Effects of Ephedrine Isomers and their Oxazolidines on locomoter activity in rats. *Gen. Pharmac.* 1993, 24:669-673. Isomers of amphetamine are also utilised.

Example 6

Inhibition of (s)-(−)-Bay K8 644 and (S-(−)-α-Methylbenzyl Isocyanate and Other Isomers with Their Respective Enantiomers or Salts Thereof in *Aspergillus Awamori*

Material and Methods

The fungal tests were carried out using *Aspergillus awamori* transformed with the aequorin gene. Aequorin is a $Ca^{2+}$ sensitive photoprotein, which emits light in the dose dependent manner when bound to free $[Ca^{2+}]$. Higher luminescence means higher concentration of intracellular calcium. Higher intracellular calcium shows that the cell is perturbed. Thus, the higher luminescence, the higher the toxicity of the compound.

*Aspergillus* cultures were grown on Vogel's medium in the presence of 1% sucrose in 96 well plates (EG & G Berthold, Bad Wildbad, Germany). Twelve ml of sterile Vogel's media with 1% sucrose was inoculated with $1 \times 10^5$ spores per ml. Coelenterazine was added in methanol (MeOH) to a final concentration of 2.5 μM. The final MeOH concentration was not more than 0.1%, which was found not to affect spore germination or hyphal growth (Nelson 1999). Using a 12-channel pipette (Anachem, Luton, UK), 100 μl of the inoculated media was added to each well, and the plate covered with a microplate lid (Labsystems, Helsinki, Finland). Cultures were incubated in a humidity chamber in the presence of free water at 30° C. for 24 h.

Luminometry was performed using an E G & G Berthold (Bad Wildbad, Germany) LB96P MicroLumat luminometer which was controlled by a dedicated PC. The luminometer measures light emission in relative lights units (RLU). To convert RLU into $[Ca^{2+}]_c$ concentrations the following empirically derived equation was used:

$$pCa = 0.332588(-\log K) + 5.5593,$$

where k=luminescence counts $s^{-1}$/total luminescence counts (Fricker et al. 1999).

The total amount of luminescence was measured as an integral of all luminescence up to complete aequorin discharge. Aequorin was discharged by adding 2 M $CaCl_2$ in 10% ethanol to the wells followed by the injection of 100 mM $CaCl_2$.

4 pairs of optical enantiomers or salts thereof of the following chemicals were used in this study:

(R)-(+)-α-Methylbenzyl isocyanate and (S)-(−)-α-Methylbenzyl isocyanate. Only freshly made stocks of α-Methylbenzyl isocyanide are effective. In the aqueous solution α-Methylbenzyl isocyanate will react with water producing α-Methyl benzyl amine and $CO_2$ and hence becomes a lot less toxic.

(R)-(+)-BAY K8644 and (S)-(−)-BAY K8644

(R)-(+)-nicotine (+)-di-p-toluoyltartrate salt and (S)-(−)-nicotine (R)-(+)-verapamil and (S)-(−)-verapamil Also a racemic mixture of (R)-(+)α-Methylbenzyl isocyanate and (S)-(−)α-Methylbenzyl isocyanate was tested.

The first substance tested was BAY K8644. The effect of preincubation of *Aspergillus awamori* with 10 μM (R)-(+)-BAY K8644 on $Ca^{2+}$ response to 10 μM (S)-(−)-BAY K8644 is shown below in FIG. 1A.

BAY K8644 was used as a simple 10 μM dilution. 10 μM (R)-(+)-BAY K8644 was used to test if there was any evidence of inhibition of the toxic effects of its enantiomer (S)-(−)-BAY K8644.

Homeopathic preparation of all compounds were as follows:

Four compounds were prepared to investigate their ability to aggravate or inhibit toxicity in certain situations. All were stored under temperature conditions recommended by Sigma Aldrich, who was the supplier.

A potency of (R)-(+)-α-Methylbenzyl isocyanate was prepared to investigate the effect on toxicity of its enantiomer, (S)-(−)-α-Methylbenzyl isocyanate. Both of these compounds are available as liquids at temperatures at which we used them, i.e., greater than 3 degrees Celsius.

A preparation of potencies of racemic α-Methylbenzyl isocyanate was prepared to investigate the effect on toxicity of the racemic α-Methylbenzyl isocyanate in toxic dose. The racemic molecule is liquid at the temperature at which we used them.

A potency of (R)-(+)-BAY K8644 was prepared to investigate the effect on toxicity of its enantiomer. To do this a solution of 2.8 mM (2.8 milli Molar) (R)-(+)-BAY K8644 in distilled water was produced, and the potency was prepared from this, as described below.

A potency of (R)-(+)-Nicotine (+)-di-p-toluoyltartrate was produced to investigate the effect on toxicity of (S)-(−)-Nicotine. Both these compounds exist in liquid form at temperatures used by us.

A potency of (R)-(+)-Verapamil hydrochloride was prepared to investigate the effect on toxicity of its enantiomer. A solution of 10 mM (10 milli Molar) (R)-(+)-Verapamil hydrochloride in distilled water was produced and the potency was prepared from this as described below.

Thirty 10 ml falcon test tubes were used to prepare the treatment and were numbered from 1 to 30. The first test tube contained 3.7 ml 35% ethanol. The remaining 29 tubes each contained 4.7 ml 35% ethanol.

All treatment compounds were prepared as per the following example with (R)-(+)-α-Methylbenzyl isocyanate starting with, 0.2 ml of respective liquid compounds, or 0.2 ml of the milli Molar concentrations quoted for (+) BAY K8644 and (+) Verapamil HCl quoted above.

On the first day 0.2 ml (R)-(+)-α-Methylbenzyl isocyanate was added to 3.7 ml 35% ethanol in a 10 ml Falcon test tube with cap. The test tube was sealed and was given 20 forceful downward successions at 1-2 Hz. One drop was removed from this test tube using a Hirschman Laborgeräte 75 mm 75 microlitre capacity non-heparinised hematocrit capillary tube, and was added to the second test tube. This was given 20 succussions as already described. One drop of the second test tube was removed and added to the third test tube and so on to produce the thirtieth potency. Each level of attenuation or potency preparation was given 20 succussions at 1-2 Hz, to produce until the $30^{th}$ potency was prepared.

Since 35% ethanol is toxic to fungi and would have confounded the experiment, to prepare the $30^{th}$ potency for use in this experiment, one drop of tube 29 was added to 4.7 ml distilled water. This was administered 20 succussions as previously described to produce a thirtieth potency in distilled water. This is the remedy H1 which was administered to counteract toxicity of the (−)-isomer in one part of the experiment. Since the stability of homeopathic preparations in water is probably poor, it is important to administer these fresh solutions in water to organisms within 30-40 minutes of their preparation.

Although the thirtieth potency of a propranolol isomer has previously been reported as being effective in counteracting the toxic effects of its enantiomer in mice (examples 2 and 3) it as not known if this potency would be suitable in *Aspergillus*. Usually in homeopathy the election of potency for a condition is largely determined by a practitioner's practical xperience, tradition, anecdote, by using Kent's octave, or by trial and error—there are no validated scientific guidelines for selection of potency. Therefore to protect against a negative result on these grounds, a second preparation of homeopathy was made called H2.

To prepare H2 the contents of test tubes 4, 12 and 30 (all prepared in 35% ethanol) were added to a 100 ml glass flask with ground glass stopper. The contents were given 20 forceful downward succussions at 1-2 Hz. One drop of the contents were removed using a hematocrit capillary tube and added to a 10 ml falcon test tube containing 4.7 ml distilled water. This test tube was then succussed 20 times as already discussed to produce H2. As with H1, this H2 potency in distilled water should be administered within 30-40 minutes of its preparation.

All homeopathic preparations were added in total volume of 25 μl of distilled water with the 10 min interval for a total period of 30 min. The other enantiomer was applied through the 100 μl injectors at the effective concentration determined by the range finder screening. Controls involved the addition of relevant placebo. All the experiments were performed at least twice with 6 replicates each. A different type of experiment was performed with (R)-(+)-BAY K8644 and (S)-(−)-BAY K8644. Cells were preincubated with a 10 μM of (R)-(+)-BAY for 5 min and then stimulated with the same concentration of (S)-(−)-BAY K8644. This was therefore a sample dilution.

For testing the racemic mixtures of (R)-(+)-α-Methylbenzyl isocyanate and (S)-(−)α-Methylbenzyl isocyanate, separate homeopathic preparations were prepared for both (R)-(+)-α-Methylbenzyl isocyanate and (S)-(−)-α-Methylbenzyl isocyanate isomers. To prepare the medicine or potency for this experiment 0.2 ml (R)-(+)-α-Methylbenzyl isocyanate was added to 3.7 ml 35% ethanol in a 10 ml Falcon test tube with cap. The test tube was sealed and was given 20 forceful downward succussions at 1-2 Hz. One drop was removed from this test tube using a Hirschman Laborgeräte 75 mm 75 microlitre capacity non-heparinized hematocrit capillary tube, and was added to the second test tube. This was given 20 succussions as already described. One drop of the second test tube was removed and added to the third test tube and so on to produce the thirtieth potency. Each level of attenuation or potency preparation was given 20 succussions at 1-2 Hz, and this process was repeated until the 30th potency was prepared. The same procedure was repeated with the (−) isomer.

One drop of 29th potency of (+) isomer was added to 4.7 ml of water. Then one drop of 29th potency of (−) isomer was added to the same tube. This was given 20 successions as already described. This is the remedy H1. For H2 remedy one drop of 4th, 12th and 30th potencies of both (−) and (+) isomers were mixed. This was given 20 successions as already described. The incubation with homeopathic preparations was performed as described above. The follow up stimulation was carried out using with 50 mg/l mixture of (R)-(+)α-Methylbenzyl isocyanate and (S)-(−)-α-Methylbenzyl isocyanate.

25 μl of all homeopathic treatment preparations were added to each culture well or replicate at 30 minutes, 20 minutes and 10 minutes prior to addition of the of the toxic enantiomer. The toxic enantiomer was applied through the 100 μl injectors at the effective concentration determined by the range finder screening. Controls involved the addition of relevant placebo, which consisted of 1 drop of 35% ethanol added to 4.7 ml distilled water in a 10 ml falcon test tube, and this was given 20 successions at 1-2 Hertz as previously discussed. The different type of experiments was performed with (R)-(+)-BAY K8644 and (S)-(−)-BAY K8644. Cells were pre-incubated with a 10 μM of (R)-(+)-BAY for 5 minutes and then stimulated with the same concentration of (S)-(−)-BAY K8644.

Results

The first experiment involved the BAY molecule and results are in FIG. 1A. It was noted that final resting level was lower in the *Aspergillus* preincubated with 10 μM (R)-(+)-BAY K8644. Since this microbial bioassay is able to measure more than one end-point, the final resting level was selected as the prospective end-point for subsequent experiments however other end points reported here were indicative of decreased toxicity in the treatment group.

FIG. 1A shows the effect of preincubation of *Aspergillus* with 10 μM (R)-(+)-BAY K8644 on $Ca^{2+}$ response to 10 μM (S)-(−)-BAY K8644. There was significant inhibition of the $[Ca^{2+}]_c$ response and therefore there was inhibition of toxicity. The underlined data represent statistically significant data according to the 5% LSD (least significant difference) where p=0.05, n=6.

Figure 1B:
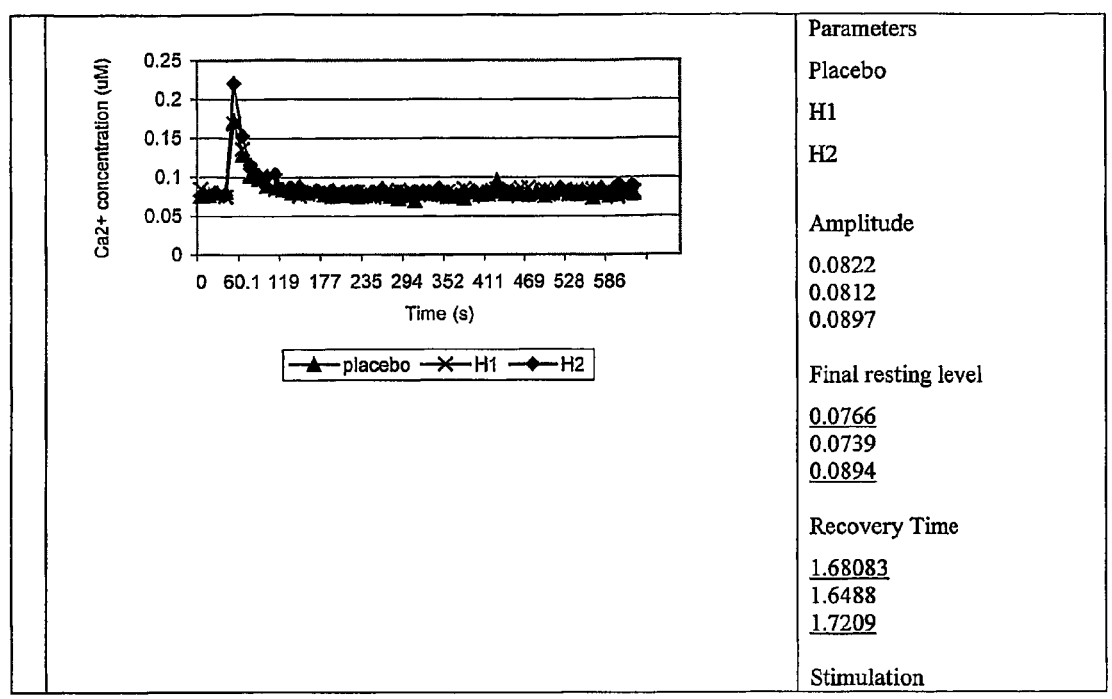
FIG. 1B shows the effect of homeopathic preparations of (R)-(+)-BAY K8644 on $[Ca^{2+}]_c$ response to 30 µM (S)-(−)-BAY K8644.

Results presented in FIG. 1B show that preincubation with 10 μM (R)-(+)-BAY K8644 caused a significant inhibition of the $[Ca^{2+}]_c$ response and therefore caused inhibition of toxicity.

Note that the first experiment with BAY shown in FIG. 1A and the subsequent experiments with α-Methylbenzyl isocyanate enantiomers, except perhaps the racemic methyl benzyl experiment were performed with strictly fresh (less than 40 minutes old) preparations in distilled water. In fact the delay before use was between 3-5 hours. Since the stability of homeopathy in water is doubtful, it is possible that the experiments which follow below, although significant, have demonstrated a diminished effect than would otherwise have been possible.

FIG. 1B shows the effect of homeopathic preparations of (R)-(+)-BAY K8644 on $[Ca^{2+}]_c$ response to 30 μM (S)-(−)-BAY K8644. H1 and H2 are homeopathic preparations. Underlined data represents statistically significant data according to the 5% LSD (least significant difference) where p=0.05, n=6. Data presented in FIG. 1B shows that homeopathic preparations of (R)-(+)-BAY K8644 causes an increase in the $[Ca^{2+}]_c$ response to 30 μM (S)-(−) BAY K8644. The increase in final resting level and recovery rate was observed. Therefore this demonstrates aggravation of toxicity.

Figure 2A:
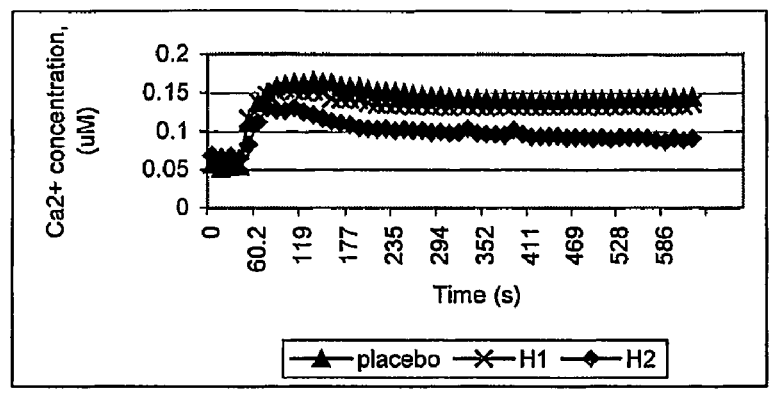
FIGS. 2A, 2B, 2C show the effect of homeopathic preparations of (R)-(+)-α-Methylbenzyl isocyanate on $[Ca^{2+}]_c$ response to 50 mg/l (S)-(−)α-Methylbenzyl isocyanate.
Figure 2B:
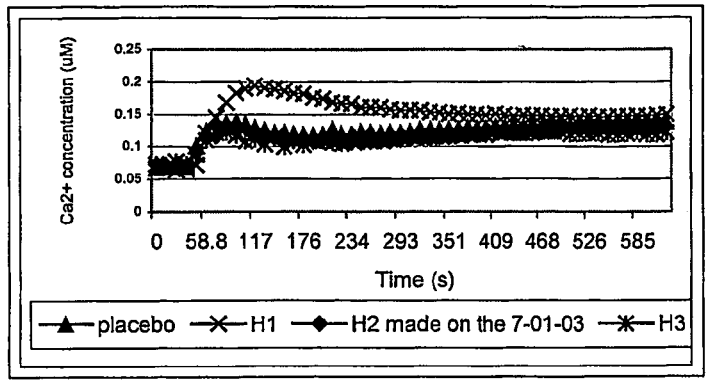
Figure 2C:
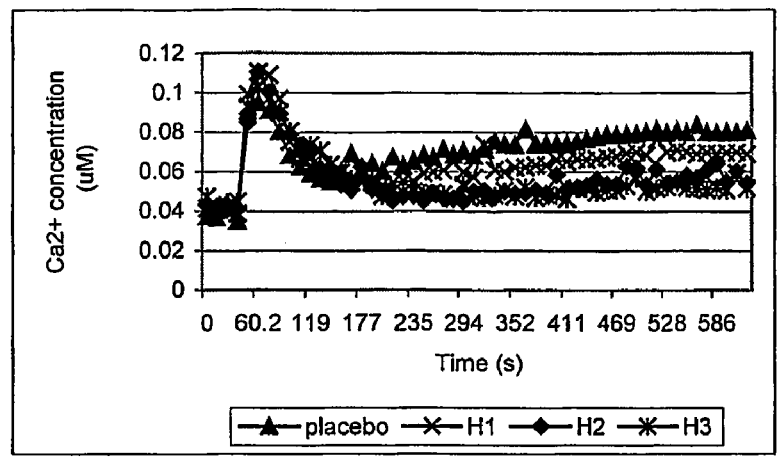

FIGS. 2A, 2B, 2C show the effect of homeopathic preparations of (R)-(+)α-Methylbenzyl isocyanide on $[Ca^{2+}]_c$ response to 50 mg/l (S)-(−)α-Methylbenzyl isocyanate. Note: H1, H2 and H3 homeopathic preparations. Underlined data represent statistically significant data according to the 5% LSD (least significant difference) where p=0.05. FIGS. 2A, 2B and 2C represent repeats of the experiment performed on different days.

The results presented in FIGS. 2A, 2B, 2C show that H1 has the most variability in its effect on $[Ca^{2+}]_c$ response to the 50 mg/l (S)-(−)α-Methylbenzyl isocyanate. H1 does not cause the inhibition of the $[Ca^{2+}]_c$ response and in one case causes the stimulation of $[Ca^{2+}]_c$ response. The variability of effect indicates that it may be possible for homeopathic preparations to increase as well as decrease toxicity, or in other words, to aggravate as well as ameliorate. This is well accepted in homeopathic theory.

The amount of variability obtained with the H2 type of preparation is much smaller. In all cases there is a significant decrease in the $[Ca^{2+}]_c$ final resting level. In most cases the recovery time of $[Ca^{2+}]_c$ is also significantly decreased. The effect on the amplitude is minimal and is only caused by the one-day-old H2. Therefore H2 was selected as the primary treatment being tested in the subsequent 2 experiments involving Methylbenzyl isocyanate.

Results in FIGS. 2A, 2B and 2C show that using final resting level as the prospective end-point, the toxicity of (S)-(−)α-Methylbenzyl isocyanate was inhibited with p<0.05 in each of 3 consecutive experiments according to the 5% least significant difference. Furthermore, the other 2 end-points reported showed trends in favour of H2 having an inhibitory effect in toxicity, and furthermore, in over 50% of cases the reported differences were statistically significant.

Figure 3:
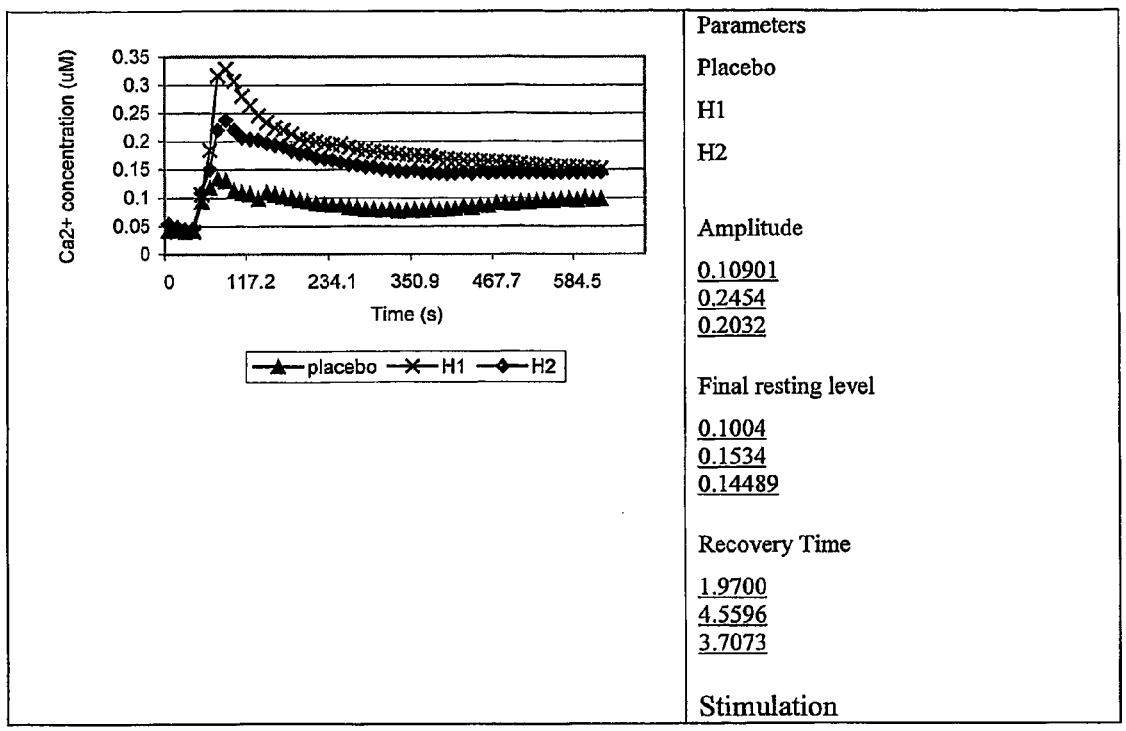
FIG. 3 is a graph showing the potencies of a racemic mixture of (R)-(+)α-Methylbenzyl isocyanate and (S)-(−)-α-Methylbenzyl isocyanate and $[Ca^{2+}]_c$ response.

The results presented in FIG. 3 shows that potencies of a racemic mixture of (R)-(+)α-Methylbenzyl isocyanate and (S)-(−)α-Methylbenzyl isocyanate caused significant increase in $[Ca^{2+}]_c$ response. Both H1 and H2 increased amplitude, resting level and recovery time of the $[Ca^{2+}]_c$ response therefore showing an increased toxicity of the racemic mixture to the fungal organism in comparison when using homeopathic preparation of (R)-(+)α-Methylbenzyl isocyanate.

Figure 4:
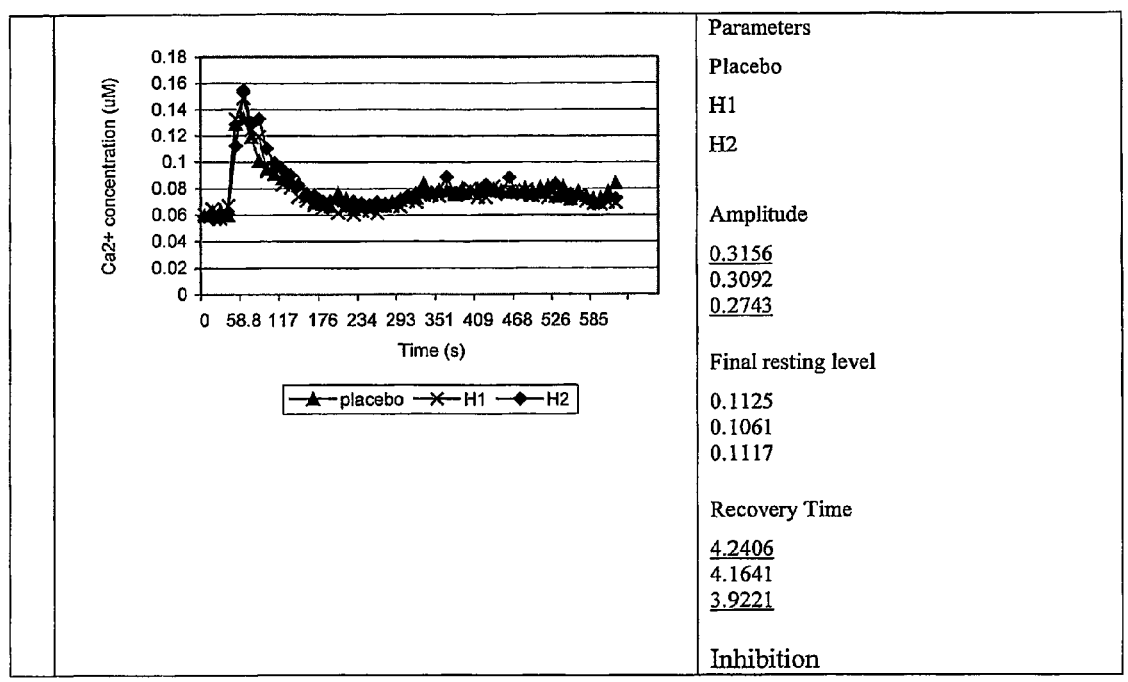
FIG. 4 shows the effect of homeopathic preparations of (R)-(+)-verapamil on $[Ca^{2+}]_c$ response to 0.33 mM (S)-(−)-Verapamil.

FIG. 4 shows the effect of homeopathic preparations of (R)-(+)-verapamil on $[Ca^{2+}]_c$ response to 0.33 mM (S)-(−)-Verapamil. Note: H1 and H2 homeopathic preparations. Underlined data represent statistically significant data according to the 5% LSD (least significant difference) where p=0.05, n=6.

Data presented in FIG. 4 shows that homeopathic preparations of (R)-(+)-Verapamil cause an inhibition of the $[Ca^{2+}]_c$ response to 0.33 mM (S)-(−)-Verapamil. The alleviation of the toxicity was observed in decrease in amplitude and recovery time.

Figure 5:
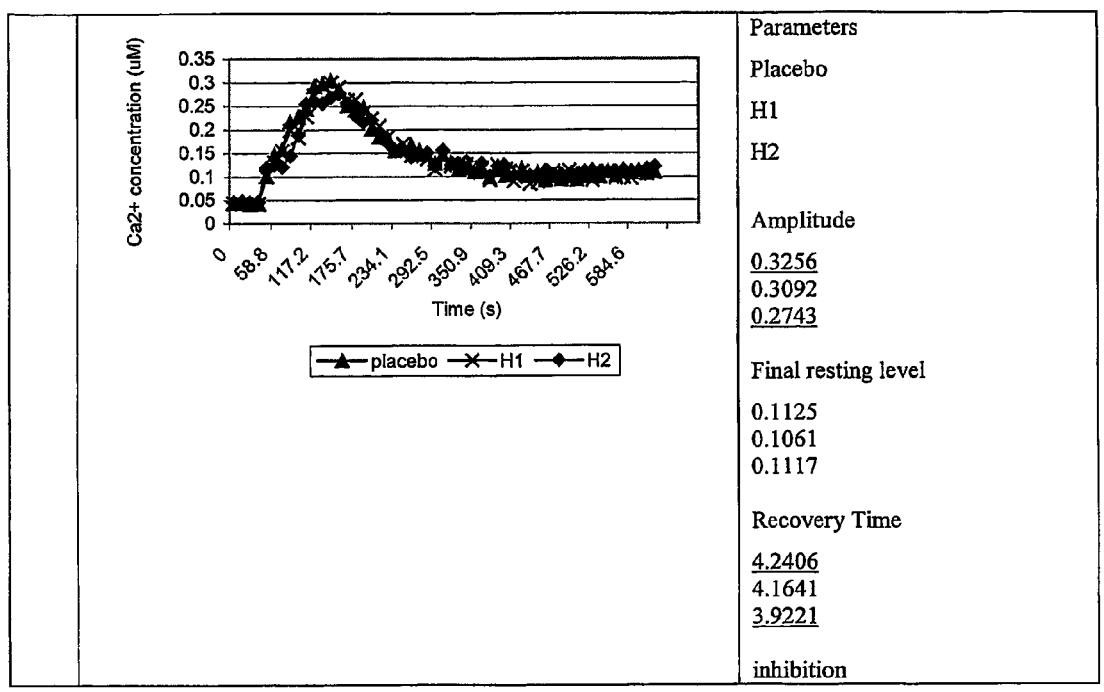
FIG. 5 shows the effect of homeopathic preparations of (R)-(+)-Nicotine (+)-di-p-toluoyltartrate sale on $[Ca^{2+}]_c$ response to 0.5% (S)-(−)-Nicotine.

FIG. 5 shows the effect of homeopathic preparations of (R)-(+)-Nicotine (+)-di-p-toluoyltartrate sale on $[Ca^{2+}]_c$ response to 0.5% (S)-(−)-Nicotine. Note: H1 and H2 homeopathic preparations. Underlined data represent statistically significant data according to the 5% LSD (least significant difference) where p=0.05, n=6.

Data presented in FIG. 5 shows that homeopathic preparations of (R)-(+)-Nicotine(+)-di-p-toluoyltartrate salt causes a stimulation in $[Ca^{2+}]_c$ response to 0.5% (S)-(−)-Nicotine. The alleviation of the toxicity was observed to decrease amplitude and recovery time.

Example 7

The Effect of Enantiomer Preparations on the Toxicity of Chemicals Using a Prokaryotic Test System Toxicity testing of various enantiomers mixtures can be done using specially designed lux-marked bacteria (multi-copy plasmid in which a gene promoter was fused with the *Vibrio fischeri* luxCDABE genes). These bacteria used are able to detect both genotoxicity and cytotoxicity in chemicals by either increased (for genotoxicity) or reduced (for cytotoxicity) light output compared to controls without chemicals. Any chemical substance that does not elicit a response will mirror light output of the control.

The bacteria are grown overnight with shaking at 27° C. in LB (Luria-Bertani) broth in the presence of antibiotic to a particular cell density. The culture is diluted with fresh sterile LB broth without antibiotic and then cultured for a further 3 hour period.

Toxicity testing is done with different concentrations of chemicals in 96-well microtiter plates in the presence of the bacterial test strain to determine inhibitory (cytotoxic) concentrations. A concentration giving inhibitory responses but not lethality is chosen for each active (−) enantiomer of the chemical for the toxicity alleviation tests.

Toxicity alleviation determination is carried out by preincubating the bacteria for 3 hours in different dilutions of the (+)-enantomer of the chemical. An overnight culture of the bacteria grown in the presence on antibiotic was diluted with fresh LB broth without antibiotic and aliquots (1 ml in a final volume of 100 ml culture) of the +enantiomer at dilutions C30, mixtures of 3 intermediate dilutions (as described elsewhere) and a control (placebo). This 1 ml addition was repeated at times 1 and 2 hour, and, after a 3 hour incubation aliquots of culture were placed in microtiter plates containing the (−) chemical concentration which previously gave inhibitory effects. Testing over over a period of time would reveal whether the (+) enantiomer reduced the inhibitory effect of the (−) enantiomer.

Light measurements can be made using an Anthos Lucy Luminometer. The experiment may also be carried out using *salmonella* species.

Chemicals which can be used for this experiment include enantiomers of BAY K8644, Verapamil HCl and alpha-Methylbenzyl isothiocyanate or alpha-Methylbenzyl isocyanate or O-Acetylmandelic acid, Ibuprofen or nicotine or any optical isomer which is toxic to the microorganism used in the bioassay which is soluble in the culture media.

Example 8

The method of the present invention is used to counteract or enhance the effects of any optically active molecules including protein (see References 1 to 4). Toxicological investigations are used to demonstrate the method (see Reference 5).

Those skilled in the art will appreciate that the invention described herein is susceptible to variations and modifications other than those specifically described. It is to be understood that the invention includes all such variations and modifications that fall within its spirit and scope. The invention also includes all of the steps, features and compositions referred to or indicated in this specification, individually or collectively, and in any and all combinations of two or more of said steps, features and compositions.

REFERENCES

1. Sempach Pty Ltd, Australian Patent—regarding drugs, proteins and other optically active molecules, 17 Sep., 2002, *The Age newspaper*, Melbourne, Australia, The Age Company Limited
2. Sempach Pty Ltd, Australian Patent—regarding drugs, proteins and other optically active molecules, 18 Sep., 2002, *The Australian*, Sydney, Australia, News Limited
3. Sempach Pty Ltd, Australian Patent—regarding drugs, proteins and other optically active molecules, 24 Sep., 2002, *The Australian Financial Review*, Sydney, John Fairfax Publications Pty Ltd
4. Sempach Pty Ltd, Australian Patent—regarding drugs, proteins and other optically active molecules, 1 Oct., 2002, *The Age newspaper*, Melbourne, Australia, The Age Company Limited
5. Sempach Pty Ltd, Advertisement in *Human and Experimental Toxicology*, Vol. 21, Number 11, Nov. 2002
6. Lovell D P, Variation in Pentobarbitone sleeping time in mice, *Laboratory Animals* 1986; 20:85-96 & 307-312
7. Special Diets Services Ltd, PO Box 705, Witham, Essex, CM8 3AD, U.K.
8. Blackie Foundation Trust, Blackie Foundation Trust Protocol, London, U.K.
9. Walker R B, Fitz D, Williams L M, The effect of ephedrine isomers and their oxazolidines on locomotor activity in rats, *Gen Pharmac.* 1993; 24:669-73
10. Hennekens, C. H. and Buring, J. E., *Epidemiology in Medicine*, 258-264, 1987, Philadelphia, Lippincott Williams & Wilkins
11. Hamilton Laboratory Glass Ltd, Europa House, Margate, Keng, England, U.K. Unit 1 Westwood Industrial Estate, Ramsgate Road
12. Kuzeff, R. M., Mecheva, R. P., and Topashka-Anchera, M. N., Inhibition of (−)-Propranolol hydrochloride by its enantiomer in white mice (2002) (Unpublished)
13. Kuzeff, R. M., Mecheva, R. P., and Topashka-Anchera, M. N., Inhibition of (−)-Propranolol hydrochloride by its enantiomer in white mice (2) (2002).
14. Nelson, G. 1999. Calcium measurement using recombidant aequorin. PhD Thesis Edinburgh University.

The invention claimed is:

1. A method of treating a human suffering from the effects of nicotine addiction, comprising the steps of:
    diluting a purified optical isomer of nicotine to provide a therapeutically effective dilution of said purified optical isomer, wherein said optical isomer is (+)-nicotine; and
    administering said therapeutically effective dilution of said purified optical isomer to the human suffering from the effects of nicotine addiction.

2. A method to counter the effects of L-glutamate in a human, comprising the steps of:
    diluting a purified optical isomer of L-glutamate to provide a therapeutically effective dilution of said purified optical isomer, wherein said optical isomer is D-glutamate; and
    administering said therapeutically effective dilution of said purified optical isomer to a human in need of such treatment.

* * * * *